United States Patent [19]

Vaughan et al.

[11] Patent Number: 4,654,419
[45] Date of Patent: Mar. 31, 1987

[54] SYNTHETIC POLYPEPTIDES AND ANTIBODIES RELATED TO EPSTEIN-BARR VIRUS NUCLEAR ANTIGEN

[75] Inventors: John H. Vaughan, La Jolla; Dennis A. Carson, Del Mar; Gary Rhodes, Leucadia; Richard Houghten, Solana Beach, all of Calif.

[73] Assignee: Scripps Clinic and Research Foundation, La Jolla, Calif.

[21] Appl. No.: 638,726

[22] Filed: Aug. 8, 1984

[51] Int. Cl.$^4$ ............................................. C07K 7/08
[52] U.S. Cl. ....................................... 530/326; 530/327
[58] Field of Search ................. 260/112.5 R; 530/326, 530/327

[56] References Cited

U.S. PATENT DOCUMENTS

| | | | |
|---|---|---|---|
| 3,959,456 | 5/1976 | Zichis | 436/812 |
| 4,224,306 | 9/1980 | Zichis | 436/812 |
| 4,407,965 | 10/1983 | Yanaihara | 260/112.5 R |
| 4,423,034 | 12/1983 | Nakagawa et al. | 260/112.5 R |
| 4,474,757 | 10/1984 | Arnon et al. | 260/112.5 R |
| 4,474,886 | 10/1984 | Willard | 436/812 |

OTHER PUBLICATIONS

Journal of Immunological Methods 67, (1984) pp. 145-156.
Proceedings of the Nat'l Acad. Sciences (1983) 80, pp. 5665-5669.
Proceedings of the Nat'l Acad. Science (1984) 81, pp. 4652-4656.

*Primary Examiner*—Delbert R. Phillips
*Attorney, Agent, or Firm*—Dressler, Goldsmith, Shore, Sutker & Milnamow, Ltd.

[57] ABSTRACT

Antigens, immunogens, inocula, antibodies, diagnostic methods and systems relating to Epstein-Barr virus nuclear antigen (EBNA) are disclosed. Each of the compounds, compositions, methods or systems contains a synthetic, random copolymer polypeptide having about 6 to about 40 residues, or an antibody containing site that immunoreacts with such a polypeptide. The polypeptide includes the five amino acid residue sequence -Gly-$R^1$-Gly-$R^2$-Gly-, wherein $R^1$ and $R^2$ are the same or different amino acid residues selected from the group consisting of Ala, Asn, Arg, Gly, Leu, Pro, Ser, and Thr, with the provision that $R^1$ and $R^2$ are not both Gly. The polypeptide contains at least 25 mole percent Gly residues, and when linked to a carrier and introduced in an effective amount into a mammalian host is capable of inducing production of antibodies that immunoreact with EBNA.

11 Claims, 5 Drawing Figures

SYNTHETIC POLYPEPTIDES AND ANTIBODIES RELATED TO EPSTEIN-BARR VIRUS NUCLEAR ANTIGEN

TECHNICAL FIELD

The present invention relates to immunogens, antigens, inocula, antibodies, methods and systems useful in the treatment and diagnosis of diseases involving Epstein-Barr virus, and its nuclear antigen.

BACKGROUND OF THE INVENTION

The Epstein-Barr virus (EBV) is a member of the herpes virus family and is the causitive agent of infectious mononucleosis (IM) in humans. EBV has also been implicated in the pathogenesis of Burkitt's lymphoma, nasopharyngeal carcinoma, and B lymphocyte neoplasms arising in immunosuppressed patients. Circumstantial evidence has also indicated a possible role for this virus in human autoimmune disease such as rheumatoid arthritis and Sjogren's Syndrome.

EBV is an extremely common environmental agent infecting 80–100 percent of the individuals around the world. The initial or primary infection may be acute or sub-clinical. This is followed by a long period during which the EBV infection is latent in B lymphocytes present in the circulating blood, lymph nodes, and spleen.

Latency is the process by which a virus is present intracellularly in an unexpressed or partially expressed state. This latency can be reactivated. Although the host factors that control latency in vivo are poorly known, there is some evidence to suggest that failure of one or more immune mechanisms is an important factor.

Cytotoxic and suppressive T cell elements of the immune response to EBV are reported to be very important in suppressing acute infection by EBV in IM. They are also important in prohibiting the uncontrolled outgrowth of B lymphocytes latently infected with EBV.

Failure of T cell suppressor mechanisms is thought to be important in allowing the emergence of African Burkitt lymphoma, nasopharyngeal carcinoma, B cell lymphomas arising as a consequence of immunosuppressive therapy used to prevent rejection of organ transplantation, and lymphomas as arising during treatments of various auto immune disorders. Epstein and Achong eds., "*The Epstein-Barr Virus.*", Spring-Verleg, Berlin, Heidelberg (1970); and Crawford et al., *Lancet*, 1355 (1980). In addition, the failure of these T cell mechanisms and consequent overgrowth of EBV-infected lymphocytes is thought to play a role in reheumatoid arthritis. Slaughter et al., *J. Exp. Med.*, 148:1429 (1978); Depper et al., *J. Immunology*, 127:1899 (1981) and Tosato et al., *N. Engl. J. Med.* 305:1238 (1981).

The serological and cell-mediated immune responses that follow primary infection by EBV are well documented and reflect the host's response to the viral antigens expressed during the course of infection. The profile of these responses as well as the detection of the antigens in tissues are becoming increasingly useful in the diagnosis of EBV-associated diseases.

The earliest EBV-associated antigen that can be detected after infection is EBV-induced nuclear antigen (EBNA). EBNA has been detected in the nucleus of latently-infected growth-transformed B lymphocytes. EBNA has also been detected in the nuclei of African Burkitt tumor lymphoblasts and anaplastic nasopharyngeal carcinoma cells.

The concentration of EBNA in cell nuclei of EBV-infected By lymphocytes fluctuates during various phases of the cell's reproductive cycle. Thus, it is believed EBNA is cyclically being synthesized and degraded. As a result of such degradation, protein fragments (polypeptides) of EBNA traverse the cellular cytoplasm and are believed to exist or be expressed on the outer membrane. However, specific EBNA degradation polypeptides have not been identified to date.

It is believed that while in or on the outer cell membrane, EBNA degradation polypeptides constitute a significant stimulus to the host's T lymphocytes and initiate the immune response that results in the production of anti-EBNA antibodies. It is also believed that the specific T cell response to B cells expressing EBNA degradation polypeptides on their surfaces may contribute to the generation of cytotoxic and suppressive T cells important in restricting growth of EBNA-containing (EBV-infected) B lymphocytes.

Thus, assays for the presence of both EBNA and anti-EBNA antibodies are of importance in several common clinical situations. In addition, a vaccine against EBV-infected B lymphocytes would also be of clinical importance.

Anti-EBNA antibodies are typically assayed using the tedious anti-complement immunofluorescence technique (ACIF). Reedman et al., *Int. J. Cancer*, 11:499–520 (1973). This assay involves fixing EBV-transformed human B cells to a microscope slide. Various dilutions of a patient's serum are then added to the fixed cells. Because anticomplementary sera may yield false-negative reactions or prozones when they are mixed with the complement (a two-stage procedure), it is essential to charge the test cell smears consecutively with serum, complement, and the anticomplement-fluorescence conjugate (a three stage procedure).

There are several problems with this assay. These include the fact that the assay is relatively insensitive and requires amplification mediated through complement. In addition, this assay is not entirely specific and may not be interpreted in patients whose serum contains antibodies to mammalian cell nuclei. Still further, quantitative results obtained using an anti-complement immunofluorescence assay are difficult to reproduce. As a consequence of these and other reasons, assays for anti-EBNA antibodies have generally been confined to a few, specialized laboratories.

The above difficulties in assaying for anti-EBNA antibodies stem from the lack of relatively pure EBNA. Purification of EBNA from mammalian cell tissue cultures is complex because of the antigen's low concentration and polymorphology. Although it is easier and less costly to use whole cells expressing EBNA, as in the current technique, the problems of specificity and reproducibility are directly tne result of using whole cells.

Genetic engineering and synthetic polypeptide technologies have recently provided solutions to the problem of manufacturing large quantities of protein and polypeptide antigens. However, both techniques are effective only if the amino acid residue sequence of the native protein is known.

The amino acid residue sequence of a natural protein can be determined from the protein itself, but this is often difficult. The gene nucleotide sequence that codes for the protein may also reveal the protein's amino acid residue sequence. However, all DNA sequences have three possible reading frames, each of which yields a different protein. Therefore, the correct reading frame must be known to deduce the correct amino acid residue sequence of a protein from its gene.

The correct reading frame of a DNA sequence coding for a protein, and therefore the protein's amino acid residue sequence, may be determined through the use of antibodies. This strategy involves manufacturing an array of protein fragments or polypeptides whose amino acid residue sequences correspond to the sequences obtained from the three possible gene products. The protein fragments or polypeptides that induce antibodies that immunoreact with the gene's natural protein product thereby indentify the gene's correct reading frame. Conversely, if antibodies to the natural protein recognize the manufactured protein fragments or polypeptides, the relationship between gene and protein is also established.

Heller, et al., *J. Virol.*, 44:311–320 (1982), reported the DNA sequence for a portion of the EBV genome that was found to contain an internal region, designated IR3, consisting of direct repeats of a hexanucleotide and two nonanucleotide sequences. They cited evidence suggesting that the sequence surrounding and including IR3 contains the gene coding for EBNA. However, since it was not known which of the three possible DNA sequence reading frames was translated, Heller, et al., supra, were not able definitely to deduce the amino acid sequence for the possible EBNA protein.

In September 1983, Hennessy and Kieff, *Proc. Natl. Acad. Sci., U.S.A.*, 80:5665–5669 (1983), reported establishing the natural reading frame for the EBV DNA sequence reported by Heller, et al., supra. Essentially, they isolated IR3 DNA, cleaved it into small random pieces and inserted the pieces into the lacZ gene of an *E. coli* expression vector such that all three EBNA gene reading frames were expressed, each in a different clone. The lacZ gene codes for beta-galactosidase, a bacterial enzyme. The IR3-lacZ gene fusion product is expressed in *E. Coli* as a fusion protein with the IR3 protein sequence inserted between amino acids 7 and 9 (8 being deleted in the construction process) of the beta-galactosidase protein molecule.

Hennessy and Kieff, identified an IR3-lacZ gene fusion that was expressing IR3 DNA in its natural reading frame by screening for fusion proteins that were recognized by anti-EBNA positive human sera. A plasmid so identified was designated pKH182-44.

To confirm that the protein expressed by pKH182-44 contained EBNA-specific antigenic determinants, Hennessy and Kieff, supra, raised antisera in rabbits against cyanogen bromide-cleaved (CNBr) IR3-galactosidase fusion protein. The CNBr fragment used as an immunogen contained 53 amino acids homologous to EBNA and 89 amino acids homologous to beta-galactosidase. These antisera recognized natural EBNA in EBV-infected cells using indirect immunofluorescence.

The results of Hennessy and Kieff appear to be dependent on the repetitive nature of the EBNA IR3 domain. The fusion protein produced by pkH182-44 contains a relatively long segment homologous with the IR3 domain (e.g. 53 amino acids). It is, therefore, not surprising that the fusion protein and CNBr fragment thereof contained antigenic determinants. Furthermore, Hennessy and Kieff did not identify which of the sequences repeated in their fragment were acting as antigenic determinants.

Although Hennessy and Keiff were able to genetically manufacture a material recognized by anti-EBNA antibodies in human serum, it would be cumbersome to use in a clinical setting because of its design. The 53 amino acid residue segment of their fusion protein that is homologous to EBNA is physically and chemically part of the beta-galactosidase protein. Its immununological properties are, therefore, influenced by those portions of the beta-galactosidase molecule from which it cannot be separated. In fact, all of the human sera used in their study reacted with beta-galactosidase, and required treatment with beta-galactosidase to adsorb and remove this reactivity before testing for specificity against the genetically manufactured protein.

Another approach to the interrelated problems of determining a gene's correct reading frame and manufacturing large quantities of pathogen-related antigens (immunogens) for clinical and diagnostic purposes is the use of synthetic polypeptide chemistry. This method of manufacturing antigens (immunogens) has an advantage over the genetic engineering methods described above. Synthetic polypeptide antigens do not contain natural protein by-products or fragments thereof, and thereby their use eliminates the possibility of unwanted cross reactivity and the need to pretreat serum samples as in the Hennessy and Kieff study.

While the general concept of preparing synthetic antigens (immunogens) and using them to induce antibodies of predetermined specificity has been described, there remains a large area of this technology that continues to defy predictability. There are at least two reasons for this. First, a synthetic antigen (immunogen) does not necessarily induce antibodies that immunoreact with the intact protein in its native environment. Second, a host's natural antibodies to a naturally occurring immunogen such as a viral protein rarely immunoreact with a polypeptide that corresponds to a short linear portion of the immunogen's amino acid residue sequence. This latter phenomenon is believed to be the result of short linear polypeptides lacking required secondary and tertiary conformational structures.

Much of the work on the binding of peptide by antibody made to proteins is summarized in a review by Benjamini, E., et al., *Current Topics in Microbiology and Immunology* 58:85–134 (1972). The role of peptide structure in antibody binding has been emphasized by Goodman, J. W., *Immunochem* 6:139–149 (1969).

Most of the studies concerned with how changes in the sequence of peptides effect antibody binding have been interpreted as indicating tnat tne structure of tne antibody combining site plays a predominant role. The effect of sequence and structural changes in these studies is intermixed and difficult to segregate. Some of these studies can equally well be explained by structural changes in antigen effecting the binding.

Antibody response at the molecular level involves binding of an antigen of defined sequence (primary structure) and in a defined conformation (secondary and tertiary structure). Immune response to protein antigens has traditionally been interpreted as being directed against primary, secondary or tertiary structue of the protein.

This classification scheme may have some validity for proteins tnat have a well defined overall structure at physiological temperatures and solutions. However, its validity is in doubt for peptide antigens that nave a more dynamic structure.

Several groups have reported structural studies of polymers of repeating sequence of glycine and alanine or glycine and serine that were synthesized as models of silk fibroins [Anderson et al., *J. Mol. Biol.* 67:459-468 (1972)] and collagen [Anderson et al., BBRC 39:802-808 (1970); Doyle et al., *J. Mol. Biol.* 51:47-59 (1970)]. The most systematic study has been that of Brack et al., *Biopolymers* 11:563-586 (1972) who reported synthesis of a series of block homopolymeric polypeptides in which the homopolymeric block repeating units had the formula $(Ala_x-Gly_y)$ wherein when $x=1$, $y=1$, 2 and 3; when $x=2$, $y=1$, 2 and 3; and when $x=3$, $y=3$.

The results reported from this latter study were that in the solid state the block homopolymers composed mostly of alanine were alpha-helical, and those containing mostly glycine were disordered. In solution, polyalanine was reported to be alpha-helical, but poly-$(Ala_2-Gly_1)$ was reported to be in beta-antiparallel form. The more glycine-rich polymers were said to have another fixed structure that was reported as neither alpha-helix nor the beta-structure.

The homopolymerized blocks of glycine and alanine reported by Brack et al. were prepared by the condensation polymerization of the di- through hexapeptide repeating units having a carboxyl-terminal glycyl residue in active ester form. Degrees of polymerization from 2 through 68 were reported for poly($Ala-Gly_2$).

Even though the solvents used in those studies were not physiologically acceptable, e.g., water or phosphate buffered saline, the results illustrate two points: (1) structural changes can occur as the sequence of a polypeptide changes, and (2) structural changes also occur during the transition from solution to solid state.

SUMMARY OF THE INVENTION

The present invention contemplates a synthetic, random copolymeric polypeptide capable of inducing the production of antibodies that immunoreact with Epstein-Barr Virus Nuclear Antigen (EBNA). The random copolymeric polypeptide contains about 6 to about 40, and preferably about 15 to about 20, amino acid residues, and includes the amino acid residue sequence, written from left to right and in the direction of amino-terminus to carboxy-terminus, represented by the formula, -Gly-$R^1$-Gly-$R^2$-Glywherein:

$R^1$ and $R^2$ designate amino acid residues which taken individually are the same or different and are selected from the group consisting of Ala, Asn, Arg, Gly, Leu, Pro, Ser and Thr, with the provision that $R^1$ and $R^2$ cannot both be Gly. The polypeptide contains at least 25 mole percent Gly residues, and is capable, when linked to a carrier and introduced in an effective amount into a mammalian host, of inducing production of antibodies that immunoreact with EBNA.

Preferred polypeptides of this invention include an amino acid residue sequence selected from the group consisting of:
(i) -Gly-Arg-Gly-Arg-Gly-;
(ii) -Gly-Asn-Gly-Leu-Gly-; and
(iii) -Gly-Ser-Gly-Ser-Gly-.

In one more preferred embodiment, $R^1$ is Ala and $R^2$ is Ala, so that the polypeptide contains the sequence -Gly-Ala-Gly-Ala-Gly-.

In another more preferred embodiment, $R^1$ is Ala and $R^2$ is Gly, so that the polypeptide contains the sequence -Gly-Ala-Gly-Gly-Gly-.

In still another more preferred embodiment, $R^1$ is Gly and $R^2$ is Ala, so that the polypeptide contains the sequence -Gly-Gly-Gly-Ala-Gly-.

A preferred amino acid residue sequence includes a sequence represented by the formulae, taken from left to right and in the direction of amino-terminus to carboxy-terminus, selected from the group consisting of:

-Arg-Ala-Arg-Gly-Arg-Gly-Arg-Gly-Arg-Gly-Glu-Lys-Arg-Pro-Met-;

-Ile-Met-Ser-Asp-Glu-Gly-Pro-Gly-Thr-Gly-Asn-Gly-Leu-Gly-Glu-;

-Pro-Gly-Ala-Pro-Gly-Gly-Ser-Gly-Ser-Gly-Pro-;

the pharmaceutically acceptable salts thereof, and antigenically related variants thereof. Also preferred are the corresponding polypeptides themselves, that is, H-Arg-Ala-Arg-Gly-Arg-Gly-Arg-Gly-Arg-Gly-Glu-Lys-Arg-Pro-Met-OH;

H-Ile-Met-Ser-Asp-Glu-Gly-Pro-Gly-Thr-Gly-Asn-Gly-Leu-Gly-Glu-OH;

H-Pro-Gly-Ala-Pro-Gly-Gly-Ser-Gly-Ser-Gly-Pro-OH;

the pharmaceutically acceptable salts thereof, and antigenically related variants thereof.

In a particularly preferred embodiment, the synthetic, random copolymer polypeptide contains about 8 to about 40, and preferably about 15 to about 20, amino acid residues and includes the before-defined -Gly-$R^1$-Gly-$R^2$-Gly- amino acid residue sequence. This polypeptide also: (a) contains at least about 50 mole percent Gly residues, (b) is capable, when linked to a carrier and introduced in an effective amount into a mammalian host, of inducing the production of antibodies that immunoreact with EBNA, (c) is capable of immunoreacting with human antibodies induced by natural EBNA, and (d) additionally includes the overlapping six amino acid residue sequence, written from left to right and in the direction of aminoterminus to carboxy-terminus, represented by the formula, -Gly-Ala-Gly-Gly-Ala-Gly-.

A particularly preferred amino acid residue sequence includes a sequence represented by the formulae, taken from left to right and in the direction of amino-terminus to carboxy-terminus, selected from the qroup consisting of:
(i) -Gly-Gly-Gly-Ala-Gly-Ala-Gly-Gly-Ala-Gly-Ala-Gly-Gly-Gly-Gly-Arg-;
(ii) -Lys-Gly-Thr-His-Gly-Gly-Thr-Gly-Ala-Gly-Ala-Gly-Ala-Gly-Ala-Gly-Ala-Gly-;
(iii) -Ala-Gly-Ala-Gly-Gly-Gly-Ala-Gly-Gly-Ala-Gly-Ala-Gly-Gly-Ala-Gly-Gly-Ala-Gly;
(iv) -Gly-Gly-Ala-Gly-Gly-Ala-Gly-Ala-Gly-Ala-Gly-Gly-Gly-Ala-Gly-;
(v) -Gly-Ala-Gly-Gly-Ala-Gly-Ala-Gly-Gly-Ala-Gly-Ala-Gly-Gly-;
(vi) -Gly-Gly-Ala-Gly-Ala-Gly-Ala-Gly-Ala-Gly-Gly-Ala-Gly-Gly-Ala-Gly-Ala-Gly-;

(vii) -Gly-Gly-Gly-Ala-Gly-Gly-Ala-Gly-Ala-Gly-Gly-Gly-Ala-Gly-Ala-Gly-;

(viii) -Ala-Gly-Gly-Ala-Gly-Ala-Gly-Gly-Gly-Ala-Gly-Ala-Gly-;

the pharmaceutically acceptable salts thereof, and antigenically related variants thereof. Also more preferred are the corresponding polypeptides themselves, that is, (i) H-Gly-Gly-Gly-Ala-Gly-Ala-Gly-Gly-Ala-Gly-Ala-Gly-Gly-Gly-Gly-Arg-OH;

(ii) H-Lys-Gly-Thr-His-Gly-Gly-Thr-Gly-Ala-Gly-Ala-Gly-Ala-Gly-Gly-Ala-Gly-Ala-Gly-OH;

(iii) H-Gly-Gly-Gly-Ala-Gly-Gly-Ala-Gly-Ala-Gly-Gly-Gly-Ala-Gly-Ala-Gly-Ala-Gly-OH;

(iv) H-Gly-Ala-Gly-Ala-Gly-Ala-Gly-Ala-Gly-Ala-Gly-Ala-Gly-OH;

(v) H-Gly-Ala-Gly-Ala-Gly-Ala-Gly-Gly-Ala-Gly-Ala-Gly-Gly-OH;

(vi) H-Gly-Gly-Ala-Gly-Ala-Gly-Gly-Ala-Gly-Ala-Gly-Ala-Gly-Gly-Ala-Gly-Ala-Gly-OH;

(vii) H-Gly-Gly-Gly-Ala-Gly-Gly-Ala-Gly-Ala-Gly-Gly-Gly-Ala-Gly-Ala-Gly-OH;

(viii) H-Ala-Gly-Gly-Ala-Gly-Ala-Gly-Gly-Gly-Ala-Gly-Ala-Gly-OH;

the pharmaceutically acceptable salts tnereof and antigencally related variants thereof.

The present invention also contemplates a synthetic multimer containing a plurality of joined synthetic polypeptide repeating units wherein at least one of the repeating units is a polypeptide as described above. The polypeptide repeating units may be joined in a head-to-tail manner by amide bonds. Alternatively, the synthetic polypeptide monomers may be joined by other than amide bonds to form a polymeric multimer such as through the use of intramolecular, interpolypeptide cysteine disulfide bonds.

In another embodiment, an effective amount of a polypeptide of this invention is used in a physiologically tolerable diluent to form an inoculum capable of inducing antibodies that immunoreact with EBNA. In addition to being used for the production of antibodies, an inoculum of this invention may be used as a vaccine in humans as a means for inducing active immunity to lymphocytes expressing EBNA or fragments thereof on their cell surface.

In still another embodiment, a receptor molecule is contemplated that contains an antibody combining site that is capable of immunoreacting with EBNA. The receptor is raised to a synthetic immunogen comprising a synthetic polypeptide described above alone or as a conjugate.

Also contemplated is a diagnostic system for assaying for the presence of EBNA. The system comprises receptor molecules as described above and an indicating means for signaling for the immunoreaction of the combining sites with EBNA.

Further contemplated is a diagnostic system for assayinq for the presence of antibody molecules to EBNA in a body component. Such a system comprises a particularly preferred, random copolymer synthetic polypeptide as described above and an indicator means for signaling the immunoreaction of the polypeptide with the antibody molecules to EBNA. In a more preferred embodiment, this system also contains a solid support comprised of a solid matrix to which the particularly preferred polypeptide is affixed. A means for identifying the isotype of the immunoreacted antibody molecules may also be included in the system.

Additionally contemplated is a preparation for passive immunization against B lymphocytes expressing EBNA on their cell surfaces. The preparation comprises an effective amount of a receptor molecule described above in a physiologically tolerable diluent. When introduced into a mammalian host, the preparation is capable of reducing the effect on the host of B lymphocytes expressing EBNA on their cell surfaces.

BRIEF DESCRIPTION OF THE DRAWINGS

In the Figures forming a portion of the disclosure of this invention.

Recognition of EBNA by anti-P60 serum was innibited by incubating anti-P60 serum diluted 1:50 with 40 micorgrams/milliliter (ug/ml) of polypeptide P60 for one hour prior to immunoblotting (lane 3). Similarly, recognition of EBNA by anti-P62 serum was inhibited by incubating anti-P62 serum diluted 1:10 with 40 ug/ml of polypeptide P62 for one hour prior to immunoblotting.

The antigenic relatedness of P60 and P62 is demonstrated in lanes 6 and 7. Lane 6 shows anti-P62 serum diluted 1:10 immunoreacting with the EBNA band. In lane 7, the immunoreactivity of anti-P62 serum with the EBNA band was inhibited by incubation with polypeptide P60 at 40 ug/ml for one hour prior to immunoblotting.

Figure 3:
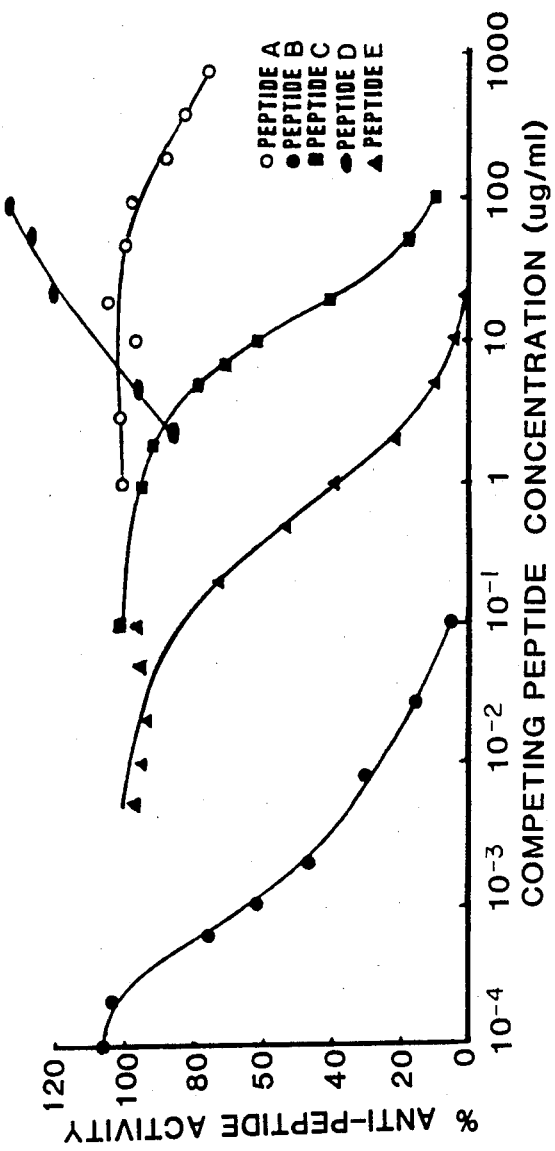

FIG. 3 is a graph illustrating the inhibition of anti-P62 serum activity in serum EBNA-positive of patient 1011 by a competing polypeptide in solution. An ELISA using polypeptide P62 as the solid phase target was performed using serum of patient 1011 pre-incubated for one hour with either of polypeptides P27, P62, P60, P89 or F16 before use in the ELISA. Polypeptides P27, P62, P60, P89 and P16 are also referred to herein as polypeptides A, B, C, D, and G, respectively. The percent anti-polypeptide activity is plotted as the ordinate versus the concentration of the competing polypeptide in micrograms/per milliliter (ug/ml).

Figure 4:
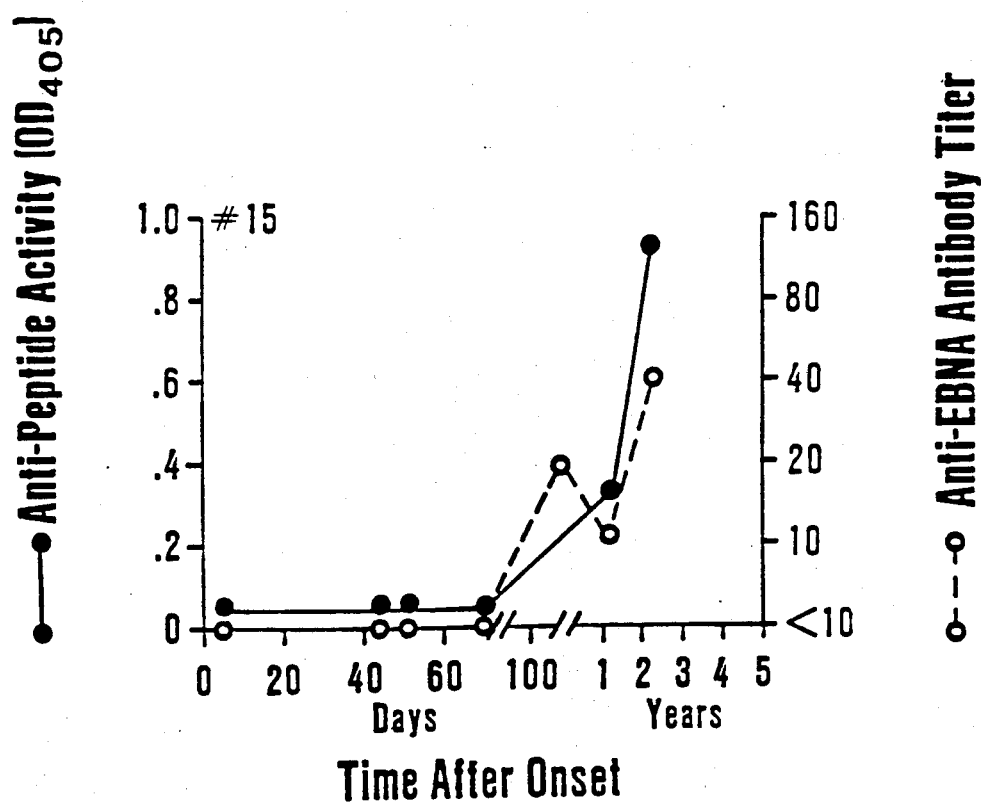

FIG. 4 is a graph that illustrates the parallel time course of appearance of antiboides to EBNA (dashed line, 0) and polypeptide P62 (solid line, ●) in a case of documented infectious mononucleosis (IM). Sequential sera were collected after clinical onset and were titered for anti-EBNA activity following the procedure reported in Catalano, et al., *J. Clin. Invest.*, 65:1238–1242 (1980) on the right-hand ordinate. The serum samples were also assayed in the ELISA of this invention using polypeptide P62 as the solid phase target as is shown on the left-hand ordinate wherein the optical density at 405 nanometers ($OD_{405}$) is plotted.

Figure 5:
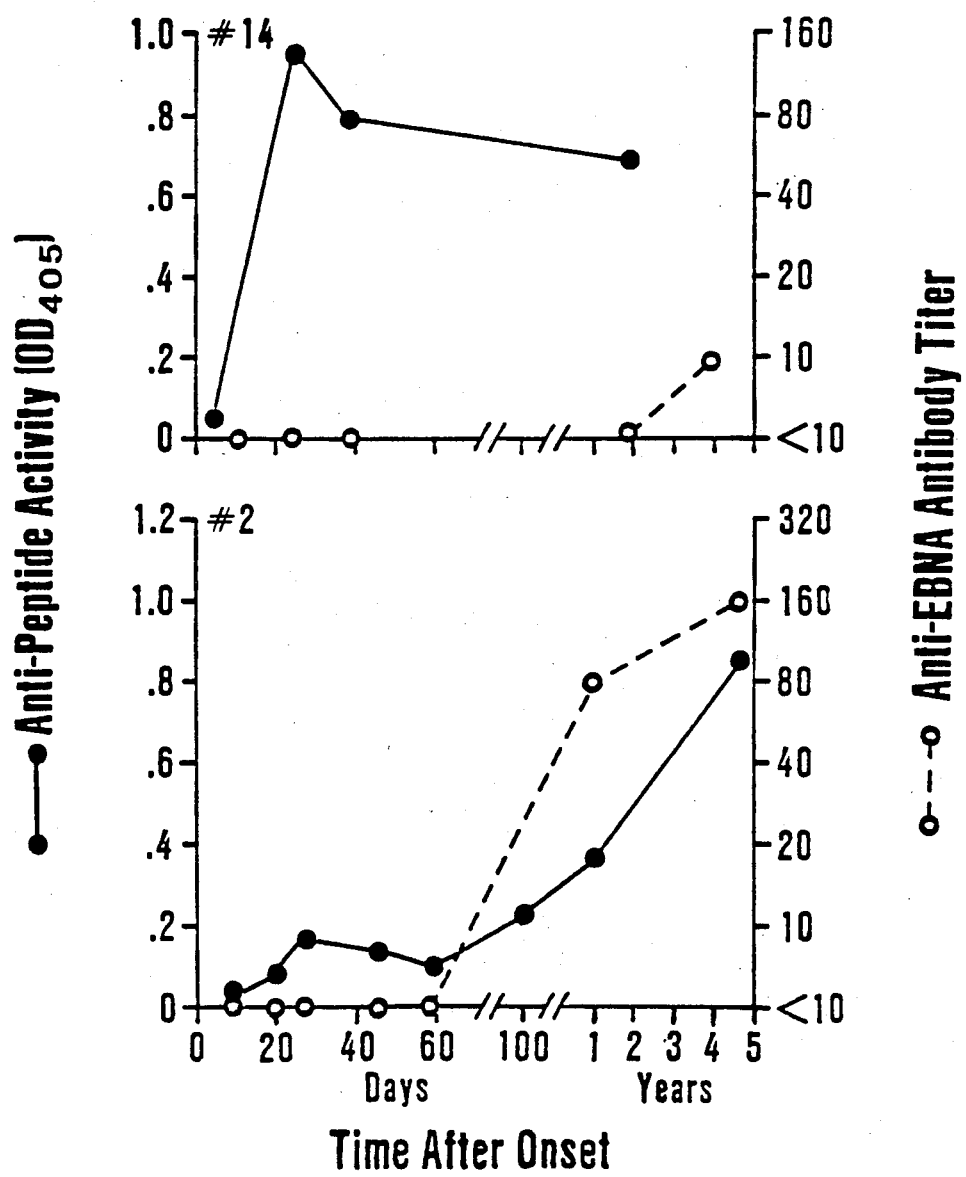

FIG. 5 is composed of two graphs that illustrate the early detection of antibodies to polypeptide P62 (solid line, ●) as compared to anti-EBNA (dashed line, 0) using detection by the classical ACIF method described by Henle, G. et al., *J. Infect. Dis.*, 130:231 (1974). Sequential sera were collected from two patients (#14 top panel, #2 bottom panel) with clinically documented infectious mononucleosis. The sera were titered for anti-EBNA activity as reported in Catalano, et al., above. Anti-polypeptide activity was measured using the ELISA of this invention using polypeptide P62 as the solid phase target, with the activity being reported as in FIG. 4.

DETAILED DESCRIPTION OF THE INVENTION

I. Introduction

Humans infected with Epstein-Barr virus (EBV) develop antibodies against a viral nuclear antigen (EBNA) that is present in virally-transformed B lymphocytes. Traditional clinical techniques used to assay for EBNA and anti-EBNA antibodies in humans are cumbersome. In addition, current procedures for the purification of EBNA from cell culture are not readily adaptable to mass production.

The present invention contemplates the use of syntnetic polypeptide technology to overcome some of the problems of the current methodologies. Short synthetic polypeptides may immunologically mimic antigenic determinants on a natural protein and may therefore be used to raise antibodies of predetermined specificity that recognize the natural protein.

The phrase "immunologically mimics" is used herein to mean that an immunogenic polypeptide of this invention induces production of antibodies that bind to the inducing polypeptide and also to the cognate sequence in the intact protein. This phenomenon may be used both experimentally and clinically.

Experimentally, antibodies to synthetic polypeptides may be used to establish the DNA reading frame, and therefore the amino acid residue sequence of a clinically important protein such as EBNA. Clinically, antibodies of predetermined specificity raised to synthetic polypeptides may be used for diagnostic and therapeutic purposes.

Heller, et. al., supra, reported a DNA nucleotide sequence with characteristics that indicated it might contain the gene coding for EBNA. They predicted that if the DNA was translated into protein, the three possible reading frames would code for an IR3 protein domain of more than 200 amino acid residues composed of only (i) serine, arginine, and glycine; (ii) glycine and alanine; or (iii) glutamine, glutamate, and glycine, depending upon the DNA reading frame expressed.

The reported chemical properties of the EBNA molecule, when taken together with the distribution of possible stop codons in the EBNA gene, indicated that the IR3 was composed primarily of glycine and alanine residues.

To assess that indication, short polypeptides were synthesized whose amino acid residue sequences substantially correspond to that of an EBNA protein whose IR3 is a glycine-alanine random copolymer.

A. Synthetic Polypeptides

1. Sequences

The series of small synthetic polypeptides (5–21 amino acid residues in length) used in this study were synthesized using the solid phase method of Merrifield. Merrifield et. al., *J. Am. Chem. Soc.*, 85:2149–2154 (1963). The sequences were chosen to represent different areas from within and just outside the proposed IR3 region of the EBNA.

The term "synthetic" as used herein means that the polypeptide molecule or polypeptide repeating unit has been built up by chemical means; i.e., chemically synthesized, rather than being prepared by a biological means, as by genetic engineering techniques. Thus, the synthetic polypeptides embodying the present invention are free from naturally occurring proteins and fragments thereof.

The chemically synthesized polypeptides also therefore differ from degradation products of naturally occurring proteins as are prepared by the action of cyanogen bromide on the protein. The well-known solid phase chemical synthesis in which blocked amino acid residues are added in a serial manner to botain the desired polypeptide is the preferred method of synthesis, and is discussed in greater detail hereinbelow.

All amino acid residues identified herein are in the natural or L-configuration. In keeping with standard polypeptide nomenclature, abbreviations for amino acid residues are as follows:

| SYMBOL | | AMINO ACID |
|---|---|---|
| 1-Letter | 3-Letter | |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

The present invention contemplates a synthetic, random copolymer polypeptide containing about 6 to about 40 amino acid residues, preferably about 15 to about 20 amino acid residues, and including the sequence defined by the formula written from left to right and in the direction of amino-terminus to carboxy-terminus -Gly-R$^1$-Gly-R$^2$-Glywherein R$^1$ and R$^2$ designate amino acid residues which when taken individually are the same or different and are Ala, Asn, Arg, Gly, Leu, Pro, Ser and Thr, provided that R$^1$ and R$^2$ are not both Gly. The polypeptide also contains at least 25 mole percent glycine residues, and is capable, when linked to a carrier and introduced in an effective amount into a mammalian host, of inducing production of antibodies that immunoreact with EBNA.

In one preferred embodiment, R$^1$ and R$^2$ are both Arg so that tne polypeptide includes the amino acid residue sequence: -Gly-Arg-Gly-Arg-Gly-. In another preferred embodiment, R$^1$ is Asn and R$^2$ is Leu so tnat the polypeptide includes the amino acid residue sequence: -Gly-Asn-Gly-Leu-Gly-. In still another preferred embodiment, R$^1$ and R$^2$ are both Ser so that the polypeptide includes the amino acid residue sequence: -Gly-Ser-Gly-Ser-Gly-.

Preferred amino acid residue sequences include the sequences, taken from left to right and in the direction of amino-terminus to carboxy-terminus, represented by the formulae:

-Arg-Ala-Arg-Gly-Arg-Gly-Arg-Gly-Arg-Gly-Glu-Lys-Arg-Pro-Met-;

-Ile-Met-Ser-Asp-Glu-Gly-Pro-Gly-Thr-Gly-Asn-Gly-Leu-Gly-Glu-

Pro-Gly-Ala-Pro-Gly-Gly-Ser-Gly-Ser-Gly-Pro-;

the pharmaceutically acceptable salts thereof, and antigenically related variants thereof.

In more preferred embodiments, R$^1$ and R$^2$ are Ala or Gly. For example, R$^1$ may be Ala and R$^2$ may be Ala; R$^1$ may be Ala and R$^2$ may be Gly; and R$^1$ may be Gly and R$^2$ may be Ala. The more preferred embodiments thus include a five amino acid residue sequence represented by a formula selected from the group consisting of
(i) -Gly-Ala-Gly-Ala-Gly-;
(ii) -Gly-Ala-Gly-Gly-Gly-; and
(iii) -Gly-Gly-Gly-Ala-Gly-.

The term "random copolymer" is used herein in its usual meaning. Thus, the polypeptides are copolymers because they contain a plurality of different amino acid residue repeating units. The copolymers are random as compared to alternating or block copolymers because the individual amino acid residues of the polypeptides are not present in a particular repeating sequence as is found in the repeating sequences of an alternating copolymer or the homoblock copolymers prepared by Anderson et al., Doyle et al., or Brack et al., supra.

Thus, even though the polypeptide denominated P62 (Table 1) that contains the sequentially repeating sequence -Ala-Gly-Ala-Gly-Gly-Gly-Ala-Gly-Gly-, that polypeptide additionally contains an -Ala-Gly-peptide at the carboxyl-terminus. As a consequence, there is no amino acid residue sequence that repeats tnroughout the polypeptide, and polypeptide P62 must be viewed as being a random copolymer and not a homoblock copolymer as are the poly(Ala$_x$-Gly$_y$) materials prepared by Brack et al. or the poly(Ser-Gly) materials prepared by Anderson et al. whose identical blocks of particular amino acid residue sequences repeat throughout the length of their polymers.

The synthetic, random copolymer polypeptides of this invention are often referred to herein simply as "polypeptides" or as "synthetic polypeptides". That usage is for brevity.

The term "antigenically related variants" is used herein to designate polypeptides of differing overall amino acid residue sequence that share at least a portion of one antigenic determinant and are therefore immunologically cross-reactive.

The term "antigenic determinant", as used herein, designates tne structural component of a molecule that is responsible for specific interaction with corresponding antibody (immunoglobulin) molecules elicited by the same or related antigen or immunogen.

The term "immunogenic determinant", as used herein, designates the structural component of a molecule that is responsible for the induction in a host of an antibody containing an antibody combining site (idiotype) that binds with the immunogen when used as an antigen.

The term "antigen", as used herein, means an entity that is bound by an antibody.

The term "immunogen", as used herein, describes an entity that induces antibody production in the host animal. In some instances, the antigen and immunogen are the same entity, while in other instances, the two entities are different.

For example, as is described hereinafter, polypeptide P62 was used to induce production of antibodies in a rabbit and thus, was used as an immunogen. The antibodies so induced bind to polypeptide P62 when used as an antigen. Polypeptide P62 was therefore both an immunogen and an antigen. Anti-EBNA antibodies bind to both EBNA the immunogen and antigen as well as to polypeptide P62 as antigen.

Preferred embodiments of the present invention are the synthetic, random copolymer polypeptides P89, F12, F13, as shown in Table 1 below, the pharmaceutically acceptable salts thereof, and antigenically related variants thereof. Each of those polypeptides contains a -Gly-R$^1$-Gly-R$^2$-Gly-amino acid residue sequence, where R$^1$ and R$^2$ are as before defined; each polypeptide contains at least about 25 mole percent Gly; and each is capable of inducing antibodies that bind to EBNA, as described before.

TABLE 1

| SEQUENCES OF SYNTHETIC POLYPEPTIDES | |
|---|---|
| Peptide* | Sequence |
| P60(C) | H—Gly—Gly—Gly—Ala—Gly—Ala—Gly—Gly—Ala—Gly—Ala—Gly—Gly—Gly—Gly—Arg—OH; |
| P89(D) | H—Arg—Ala—Arg—Gly—Arg—Gly—Arg—Gly—Arg—Gly—Glu—Lys—Arg—Pro—Met—OH; |
| F12(E) | H—Ile—Met—Ser—Asp—Glu—Gly—Pro—Gly—Thr—Gly—Asn—Gly—Leu—Gly—Glu—OH; |
| F13(F) | H—Pro—Gly—Ala—Pro—Gly—Gly—Ser—Gly—Ser—Gly—Pro—OH; |
| P27(A) | H—Lys—Gly—Thr—His—Gly—Gly—Thr—Gly—Ala—Gly—Ala—Gly—Ala—Gly—Gly—Ala—Gly—Ala—Gly—OH; |
| P62(B) | H—Ala—Gly—Ala—Gly—Gly—Gly—Ala—Gly—Gly—Ala—Gly—Ala—Gly—Gly—Gly—Ala—Gly—Gly—Ala—Gly—OH; |
| F14 | H—Gly—Gly—Ala—Gly—Gly—Ala—Gly—Gly—Ala—Gly—Gly—Gly—Ala—Gly—OH; |
| F15 | H—Gly—Ala—Gly—Gly—Ala—Gly—Ala—Gly— |

TABLE 1-continued
SEQUENCES OF SYNTHETIC POLYPEPTIDES

| Peptide* | Sequence |
|---|---|
| | Gly—Gly—Ala—Gly—Gly—Ala—Gly—Gly—OH; |
| F16(G) | H—Gly—Gly—Ala—Gly—Ala—Gly—Gly—Ala—Gly—Ala—Gly—Gly—Ala—Gly—Ala—Gly—Gly—Ala—Gly—Ala—Gly—OH; |

*Parenthesized capital letters are used to designate the corresponding polypeptide in some of the Figures and Tables herein.

The results of polypeptide/anti-polypeptide receptor binding and binding inhibition studies are discussed hereinafter in section I D. Those results, illustrate cross-reactivities and cross-inhibitory effects that parallel the amount of sequence homology among the polypeptides. For example, polypeptide P60 contains a 10 amino acid segment homologous with P62. Polypeptide P27 contains an 8 amino acid segment homologous to polypeptides P60, P62 and D1 (Table 2). Polypeptide D2 (Table 2) contains a seven amino acid residue segment homologous to segments of polypeptides P27, P60, P62 and D1. Polypeptide P89 which did not significantly crossreact in the study, contains no sequence homology with polypeptides P27, P62, and P60.

More importantly, the 8 amino acid residue sequence shared by polypeptides P27, P62, P60 and D1 contains at least one antigenic determinant common to all three random copolymer polypeptides, thereby making those three polypeptides antigenically related varients. In addition, the shared segment includes the six amino acid residue sequence -Gly-Ala-Gly-Gly-Ala-Glyand an overlapping sequence represented by the formula -Gly-R$^1$-Gly-R$^2$-Gly- wherein R$^1$ and R$^2$ are both Ala; i.e., -Gly-Ala-Gly-Ala-Gly-.

By "overlapping", it is meant that the second-named sequence is contained in part of the first-named sequence. This overlapping of amino acid residue sequence is illustrated for polypeptide P62 by the overlapping, "boxed", sequence portions shown below in which the single letter amino acid residue code is used.

G—G—G—A—G—G—A—G—A—G—G—G—A—G—G

Synthetic, random copolymer polypeptides that contain both the shared six amino acid residues-containing sequence and the overlapping five amino acid residue constitute a still more, particularly, preferred embodiment of this invention. In such particularly preferred embodiments, the synthetic, random copolymer polypeptide of the present invention contains about 8 to about 40, and preferably about 15 to about 20, amino acid residues and includes, in addition to the before defined -Gly-R$^1$-Gly-R$^2$-Gly- amino acid residue sequence, the sequence, written from left to right and in the direction of amino-terminus to carboxy-terminus, represented by the formula, -Gly-Ala-Gly-Gly-Ala-Gly-, contains at least about 50 mole percent Gly residues and is capable of both (a) inducing the production of antibodies that immunoreact with EBNA when linked to a carrier and introduced in an effective amount into a mammalian host, and (b) immunoreacting with human antibodies induced by natural EBNA.

Particularly preferred amino acid residue sequences include the sequences, taken from left to right and in the direction of amino-terminus to carboxy-terminus, represented by the formulae:

(i) -Gly-Gly-Gly-Ala-Gly-Ala-Gly-Gly-Ala-Gly-Ala-Gly-Gly-Gly-Gly-Arg-;
(ii) -Lys-Gly-Thr-His-Gly-Gly-Thr-Gly-Ala-Gly-Ala-Gly-Ala-Gly-Gly-Ala-Gly-Ala-Gly-;
(iii) -Ala-Gly-Ala-Gly-Gly-Gly-Ala-Gly-Gly-Ala-Gly-Ala-Gly-Gly-Ala-Gly-Gly-Ala-Gly-;
(iv) -Gly-Gly-Ala-Gly-Gly-Ala-Gly-Gly-Ala-Gly-Ala-Gly-Gly-Gly-Ala-Gly-;
(v) -Gly-Ala-Gly-Gly-Ala-Gly-Ala-Gly-Gly-Ala-Gly-Gly-Ala-Gly-Gly-;
(vi) -Gly-Gly-Ala-Gly-Ala-Gly-Gly-Ala-Gly-Ala-Gly-Gly-Ala-Gly-Gly-Gly-Ala-Gly-Ala-Gly-;
(vii) -Gly-Gly-Gly-Ala-Gly-Gly-Ala-Gly-Ala-Gly-Gly-Ala-Gly-Ala-Gly-;
(viii) -Ala-Gly-Gly-Ala-Gly-Ala-Gly-Gly-Gly-Ala-Gly-Ala-Gly-;

pharmaceutically acceptable salts thereof, and antigenically related variants thereof.

It is noted that a dash at the beginning or end of an amino acid residue sequence indicates a bond to a radical such as H and OH, at the amino- and carboxy-termini, respectively, or a further sequence of one or more amino acid residues up to a total of forty amino acid residues in the polypeptide chain.

Also particularly preferred are the corresponding polypeptides themselves, that is, polypeptides P60, P27, P62, F14, F15, and F16 shown in Table 1 and D1 and D2 shown in Table 2, and the pharmaceutically acceptable salts thereof and antigenically related variants thereof.

The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. The phrase also includes non-toxic acid addition salts that are generally prepared by reacting the compounds of this invention with a suitable organic or inorganic acid. Representative salts include the hydrochloride, hydrobromide, sulfate, bisulfate, acetate, oxalate, valerate, oleate, laurate, vorate, benzoate, lactate, phosphate, tosylate, citrate, maleate, fumarate, succinate, tartrate, and the like.

2. Size

The effect of changing the size of the synthetic polypeptide on its ability to be bound by anti-EBNA antibodies was studied. It was generally found that as polypeptide size is decreased, its ability to be bound by antibodies also decreased.

Polypeptide P62 consists of 20 amino acid residues of which the first nine residues from the amino-terminus are directly repeated, as shown in Table 2 using the single letter code for amino acid residues. A series of polypeptides homologous to P62 was synthesized in which amino acid residue triads were deleted from the amino-terminus of the preceding peptide to provide polypeptides D1, D2 and D3 as are shown in Table 2, below. Increasing portions of the sequence symmetry of P62 are therefore missing in polypeptides D1, D2 and D3.

TABLE 2

| Polypeptide Designation | Amino Acid Residue Sequence# |
|---|---|
| P62: | A G A G G G A G G* A G A G G G A G G A G |
| D1: | G G G A G G A G A G G G A G G A G |
| D2: | A G G A G A G G G A G G A G |
| D3: | A G A G G G A G G A G |
| A5: | G G G A G |
| A6: | A G G G A G |
| A7: | G A G G G A G |
| A8: | A G A G G G A G |
| A9: | G A G A G G G A G |

Polypeptide sequences using the single letter code are shown in the direction from left to right and from amino-terminus to carboxy-terminus.
*Junction of 9-mer direct repeat in polypeptide P62.

The ability of the D series of polypeptides to immunoreact with 3 human anti-EBNA sera and rabbit anti-P62 serum was studied using the polypeptides in the solid phase of the ELISA, described hereinafter. Antibody binding to D1 was nearly the same as that to the parent polypeptide P62 for all sera tested. In contrast, there was no binding to solid phase D3 for any serum except rabbit anti-P62. The results for D2 were intermediate and were dependent upon the serum tested. Thus, antibody recognition of this series of polypeptides was decreased as polypeptide length was shortened from 20 to 11 amino acid residues.

The fact that antibody binding fell off for all the antisera argues against the possibility that a specific antigenic determinant was being deleted by the sequential elimination of amino acid residues since the polypeptides contained two antigenic determinants, only one of which was affected by the sequence deletions. Also, the sequence symmetry of P62 assured that all sequences of four to eight amino acid residues that were present in P62 were also in D3, with the exception of those across the juncton of the repeat.

Conformational changes in the polypeptides bound to the solid support in the ELISA may have contributed to the suppression of antibody recognition. This possibility was studied by inhibiting the binding (immunoreacting) of several sera to solid phase-bound P62 by use of varying concentrations of competing polypeptides in solution. The antisera were admixed and maintained (incubated) with polypeptide P62, D1, D2 or D3 in solution for a predetermined time sufficient for immunoreaction (binding) to occur before being added to a microtiter plate coated with P62. The results of this study with sera from five patients are summarized in Table 3 below.

TABLE 3

Concentration of Competing Polypeptides Providing 50% Inhibition of Antibody Binding to Peptide P62*

| Sera | Competing Peptide (micrograms per milliliter) | | | |
|---|---|---|---|---|
| | P62 | D1 | D2 | D3 |
| TJ | 0.05 | 0.05 | 0.1 | 200 |
| VM | 0.3 | 0.3 | 0.4 | 3 |
| CV | 0.1 | 0.1 | 0.1 | 10 |
| N6 | 0.6 | 0.6 | 0.6 | 3 |
| JC | 1 | 1 | 1 | 500 |

*The ELISA procedures used for these determinations are described hereinafter in sections IE(2) and IID.

The inhibitory action of polypeptide D1 on antibody binding to P62 is considered indistinguishable from the inhibitory effect of P62 itself. This is true for all sera tested.

More interestingly, polypeptide D3 inhibited some of the sera, VM and N6, about as well as the larger polypeptides did. This strong inhibitory effect occurred despite the face that neither of those sera showed any binding to D3 bound to the solid support in the ELISA. These data are believed to indicate that the polypeptide muct be of a certain minimum length, at least about 15 amino acid residues, to maintain required secondary structure when bound to the plastic surface of a microtiter plate.

The minimum antigen size necessary for recognition was further studied using polypeptides A5, A6, A7, A8 and A9. As shown in Table 2, polypeptide A5 has five amino acid residues, and each member of the series A6-A9 was increased in length by one amino acid residue over the preceding polypeptide up to the nine residues present in A9. No antiserum tested immunoreacted with these polypeptides when they were bound to microtiter plates in the ELISA described hereinafter.

The data for ability of the A series polypeptides to inhibit binding of human anti-EBNA antibodies to solid phase P62 is shown in Table 4 below.

TABLE 4

Inhibition of Antibody Binding to Peptide P62 By 100 micrograms per milliliter Competing Peptide*

| Sera | Percent of Uninhibited Activity | | | | |
|---|---|---|---|---|---|
| | A5 | A6 | A7 | A8 | A9 |
| TJ | 96 | 80 | 91 | 74 | 31 |
| VM | 93 | 81 | 51 | 17 | 9 |
| CV | 92 | 93 | 93 | 72 | 20 |
| JC | 94 | 92 | 60 | 88 | 74 |
| S62 | 86 | 96 | 89 | 95 | 78 |
| S60 | 106 | 109 | 93 | 84 | 53 |

*These studies were carried out as described for Table 3.

Almost all sera tested were inhibited by A9 although very high concentrations were required (more than 100-fold higher than the concentrations of P62 or D1 needed for equivalent inhibition). In addition, three sera immunoreacted with and were inhibited by A8 and one by A7. None were inhibited by the shorter polypeptides A6 and A5.

Thus, the decrease in immunoreactivity that parallels a decrease in polypeptide size appears to be due to two effects: (1) the effect of deletion of the site on the antigen to which the antibody binds as shown by the A series polypeptides and, (2) the change in the conformation of the polypeptide as its size decreases as shown by the D series polypeptides.

3. Conformation

The conformational properties of the synthetic polypeptides of this invention were studied using circular dichroism (CD) spectroscopy. The CD spectra of polypeptides P27, P60, P62, F13, F15 and F16 were determined. The data, partially shown in FIG. 1, indicate that the polypeptides of this invention which include both of the preferred amino acid residue sequences; i.e.,

-Gly-R$^1$-Gly-R$^2$-Glywherein R$^1$ and R$^2$ are as described before, and

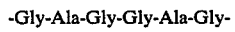
-Gly-Ala-Gly-Gly-Ala-Glyadopt a relatively stable secondary structure or conformation in a physiological solution at 20° C. Since the predominant conformation of those polypeptides is relatively stable, it is believed that human anti-EBNA antibody activity occurs in response to this particular conformation.

B. Multimers

The present invention also contemplates a synthetic multimer containing a plurality of joined synthetic, random copolymer polypeptide repeating units wherein at least one of the repeating units is a polypeptide as described herein.

The multimers of this invention, alone or linked to a carrier, when introduced in an effective amount into a mammalian host, are capable of inducing the production of antibodies that bind to EBNA. Those multimers that contain the particularly preferred synthetic, random copolymer polypeptides of this invention whose amino acid residue sequences include both the five residue -Gly-$R^1$-Gly-$R^2$-Gly- sequence, wherein $R^1$ and $R^2$ are before-defined, the six residue -Gly-Ala-Gly-Gly-Ala-Gly- sequence, and also contain at least 50 mole percent glycine residues are also capable of binding human antibodies induced by EBNA.

Thus, the multimers of this invention, like their constituent polypeptides, are immunogenic, and are antigenic to human anti-EBNA antibodies. Those multimers may therefore be used to induce the production of anti-EBNA antibodies that are useful in the diagnostic methods and systems discussed hereinafter, and may also be used as an antigen in appropriate diagnostic methods and systems.

Multimers that contain fewer than about 35 amino acid residues in the total multimer are typically linked to a carrier for use as an immunogen. Those multimers that contain more than a total of about 35 amino acid residues are typically sufficiently immunogenic to be used without a carrier.

Polypeptide multimers may be prepared by bonding together the synthesized polypeptide monomers in a head-to-tail manner using the aforementioned solid phase method; i.e., one complete polypeptide sequence can be synthesized on the resin, followed by one or more of the same or different polypeptide sequences, with the entire multimeric unit thereafter being cleaved from the resin and used as described herein. Such head-to-tail polypeptide multimers preferably contain about 2 to about 4 polypeptide repeating units.

Alternatively, multimers can be prepared as a polymer of synthetic, random copolymer polypeptides used as monomers. As used herein, the term "polymer" in its various grammatical forms is defined as a type of multimer that contains a plurality of synthetic, random copolymer polypeptide repeating units that are joined together by other than peptide bonds.

An exemplary polymer of this invention can be synthesized using the polypeptide monomers of this invention that contain added cysteine residues at both the amino- and carboxy-termini (diCys polypeptide). The diCys polypeptide monomers may be bonded together by intramolecular, interpolypeptide cysteine disulfide bonds utilizing an oxidation procedure to form an immunogenic, antigenic polymer. The polymer so prepared contains a plurality of the synthetic, random copolymer polypeptides of this invention as repeating units. Those repeating units are bonded together by the above-discussed oxidized cysteine (cystine) residues.

The presence of one or two terminal Cys residues in a polypeptide of this invention for the purposes of binding the polypeptide to a carrier or for preparing a polymer is not to be construed as altering the amino acid sequence of polypeptide repeating units of this invention.

C. Inocula

In another embodiment, the polypeptides of this invention are used in a pharmaceutically acceptable diluent to form an inoculum or a vaccine that, when administered in an effective amount, is capable of inducing antibodies that immunoreact with EBNA.

The word "inoculum" in its various grammatical forms is used herein to describe a composition containing a polypeptide of this invention as an active ingredient used for the preparation of antibodies against EBNA. When a polypeptide is used to induce antibodies it is to be understood that the polypeptide may be used alone, linked to a carrier or as a multimer, but for ease of expression, these alternatives will not always be expressed hereinafter.

For polypeptides that contain fewer than about 35 amino acid residues, it is preferable to use a carrier for the purpose of inducing the production of antibodies. A polypeptide bound or linked to a carrier will be used illustratively herein where antibodies are being prepared.

The inoculum can be used to produce antibodies for use in a diagnostic assays that detect cells expressing EBNA. The antibodies produced by the inoculum may also be used in a preparation for inducing passive immunity against B lymphocytes expressing EBNA on their cell surfaces.

The word "vaccine" in its various grammatical forms is used herein to describe a type of inoculum containing a polypeptide of this invention as an active ingredient that is used to induce active immunity in a host mammal. Since active immunity involves the production of antibodies, a vaccine or inoculum may thus contain identical ingredients, but their uses are different. In most cases, the ingredients of a vaccine and of an inoculum are different because many adjuvants useful in animals may not be used in humans.

The present inoculum or vaccine contains an effective amount of a polypeptide of this invention, as a multimer such as a polymer of individual polypeptides linked together through oxidized, polypeptide terminal cysteine residues or as a conjugate linked to a carrier. However, for ease of expression, the various embodiments of the polypeptides of this invention are collectively referred to herein by the term "polypeptide," and its various grammatical forms.

The effective amount of polypeptide per unit dose depends, among other things, on the species of animal inoculated, the body weight of the animal and the chosen inoculation regimen as is well known in the art. Inocula and vaccines typically contain polypeptide concentrations of about 10 micrograms to about 500 milligrams per inoculation (dose). The stated amounts of polypeptide refer to the weight of polypeptide without the weight of a carrier, when a carrier is used. Specific, exemplary inocula are described hereinafter with weight of carrier plus polypeptide (conjugate) being given.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on (a) the unique characteristics of the active material and the particular therapeutic effect to be achieved, and (b) the limitations inherent in the art of compounding such active material for therapeutic use in animals, as disclosed in detail in the specification, these being features of the present invention.

Inocula are typically prepared from the dried solid polypeptide-conjugate or polypeptide polymer by suspending the polypeptide-conjugate or polypeptide polymer in a physiologically tolerable (acceptable) diluent such as water, saline or phosphate-buffered saline.

Inocula may also include an adjuvant. Adjuvants such as complete Freund's adjuvant (CFA), incomplete Freund's adjuvant (IFA) and alum are materials well known in the art, and are available commercially from several sources.

D. Receptors

Antibodies and substantially whole antibodies raised to (induced by) the polypeptides of this invention as well as antibody combining sites prepared from such antibodies constitute still another embodiment of this invention. These molecules are collectively referred to herein as receptors. Receptors are raised in mammalian hosts such as mice, rabbits, horses and the like by immunization using the inocula described hereinabove.

Suitable monoclonal receptors, typically whole antibodies, may also be prepared using hybridoma technology described by Niman et. al., *Proc. Natl. Sci., U.S.A.*, 80:4949–4953 (1983), which description is incorporated herein by reference. Briefly, to form the hybridoma from which the monoclonal receptor is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653 (ATCC CRL 1580), and Sp2/0-Ag14 (ATCC CRL 1581).

Spleenocytes are typically fused with myeloma cells using polyethylene glycol (PEG) 1500. Fused hybrids are selected by their sensitivity to HAT. Hybridomas producing the receptor molecules of this invention are identified using the enzyme linked immunosorbent assay (ELISA) described in the Materials and Methods section II D hereinafter.

Monoclonal receptors need not only be obtained from hybridoma supernatants, but may also be obtained in generally more concentrated form from ascites fluid of mammals into which the desired hybridoma has been introduced. Production of monoclonal antibodies using ascites fluid is well known and will not be dealt with further herein.

A receptor of this invention binds both to the polypeptide to which it was raised and also binds to the corresponding EBNA antigenic determinant site the polypeptide of this invention immunologically mimics. Thus, a polypeptide of this invention may be both an immunogen and an antigen.

The receptors of this invention may be described as being oligoclonal as compared to naturally occurring polyclonal antibodies since they are raised to an immunogen having relatively few epitopes as compared to the epitopes of an intact EBNA molecule. Consequently, receptors of this invention bind to epitopes of the polypeptide while naturally occurring antibodies raised to EBNA bind to epitopes throughout the EBNA molecule.

Exemplary receptor molecules containing antibody combining sites of this invention raised in rabbits to the polypeptides shown in Table 1 were studied using the immunoblotting procedures of Towbin, et. al., *Proc. Natl. Acad. Sci., U.S.A.*, 76:4350–4354 (1979) and Billings, et. al., *Proc. Natl. Acad. Sci.*, U.S.A., 80:7104–7108 (1983). Further details are provided in the Materials and Methods section (II).

It was found that all the polypeptides of this study elicited rabbit anti-polypeptide antibodies when linked to a protein carrier as a conjugate and introduced in an effective amounts into rabbit hosts in an inoculum as described hereinafter. These receptor molecules recognized intact EBNA protein isolated from the EBV-transformed human B lymphoblast cell lines WI-L2, Raji and Daudi. Data from these studies are partially shown in FIG. 2. In control studies, protein extracts of B lymphocytes negative for EBV infection (BJAB cells; available at the Scripps Clinic and Research Foundation, La Jolla, CA) failed to yield reactive bands with the anti-polypeptide antisera. These data indicate that exemplary receptor molecules of this invention immunoreact with an EBV infection-specific protein.

Figure 2:
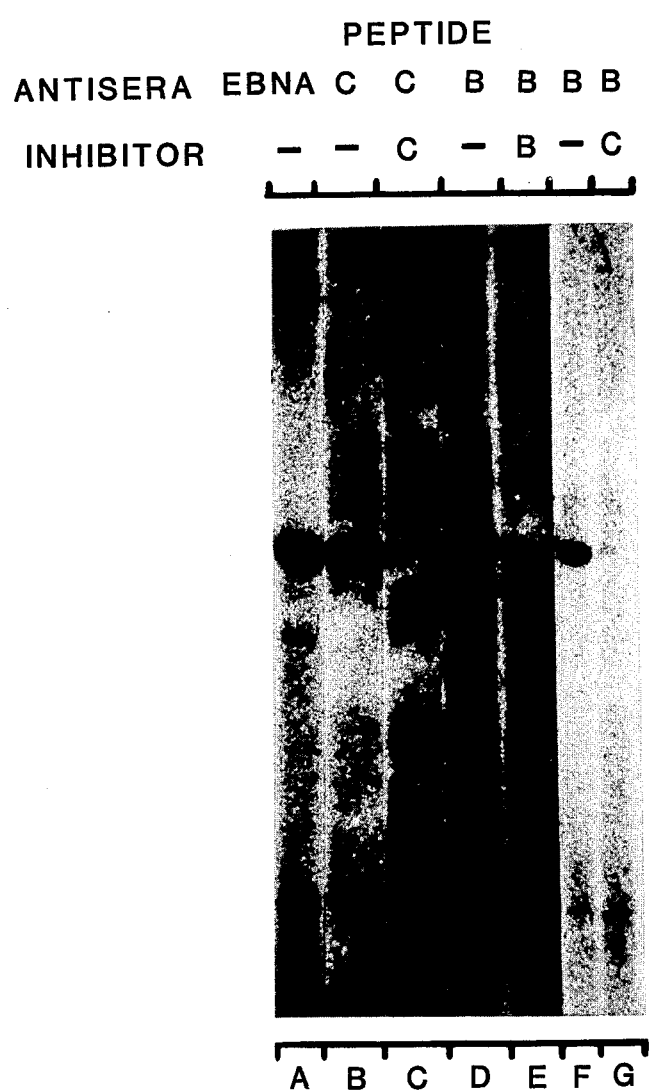
FIG. 2 is a photograph of nitrocellulose immunoblots of whole cell extracts of EBV-transformed WI-L2 cells using rabbit antipeptide antisera to synthetic polypeptides C (P60) and B (P62). A human serum (from patient TJ) previously defined as anti-EBNA positive; i.e., containing anti-EBNA antibodies, was used as a positive control in lane A at a 1:20 dilution. Rabbit anti-P60 (C) serum at a 1:50 dilution (lane B) and rabbit anti-P62 (B) serum at 1:10 (lane D) immunoreacted with tne same band as the positive control indicating they recognize natural EBNA. Lanes A–G are identified at the bottom of the Figure.

In addition, it was found that the immunoreactivity of the rabbit anti-polypeptide antibodies for intact EBNA protein could be blocked by the inducing, immunogenic polypeptide used as an antigen, as is also shown in FIG. 2. These results demonstrate that the idiotypes (antibody-combining sites) of the anti-polypeptide antisera were specific for EBNA antigenic determinants.

The rabbit anti-polypeptide antibody to polypeptide P62 was used in a competition study to examine the antigenic relatedness of polypeptides P27, P62, P60 and P89. This antibody cross-reacted extensively with the conjugated and non-conjugated polypeptides in the ELISA described hereinafter. The binding of anti-polypeptide P62 to polypeptide P62 in the solid phase was inhibited 98 percent by first incubating the antibody with polypeptide P62. In the same manner, the binding of anti-polypeptide P62 to polypeptide P62 was inhibited 81% by polypeptide P60, and 36% by polypeptide P27. Polypeptide P89 did not inhibit anti-polypeptide P62 reactivity at all.

To determine whether or not the antibodies in human EBV-immune serum also recognized this antigenic determinant, a competition study was performed using the serum of an EBV-immune, rheumatoid arthritis patient (serum 1011). The results, shown in FIG. 3, were similar to those obtained when anti-polypeptide-P62 was used. This indicates that the antigenic determinant shared by polypeptides P27, P62 and P60 mimics a naturally occuring immunogenic determinant of EBNA.

E. Diagnostic Assays Systems and Methods

The polypeptides, antibodies and antibody combining sites (receptors) raised to the before described polypeptides, and methods of the present invention may also be used for diagnostic tests, such as immunoassays. Such diagnostic techniques include, for example, enzyme immune assay, enzyme multipled immunoassay technique (EMIT), enzyme-linked immunosorbent (ELISA), radio-immune assay (RIA), flourescence immune assay, either single or double antibody techniques, and other techniques in which either the receptor or the antigen is labeled with some detectable tag or indicating means. See generally Maggio, *Enzyme Immunoassay*, CRC Press, Cleveland, Ohio (1981); and Goldman, M., *Flourescent Antibody Methods*, Academic Press, New York, N.Y. (1980). Specific examples of such assay methods and systems useful in carrying out those methods are discussed hereinbelow.

1. Assays For EBNA

A method for assaying for the presence of EBNA in a body sample is also contemplated herein. In a general method, a body sample to be assayed is provided, and is admixed with receptor molecules that contain an antibody combining site raised to a synthetic, random copolymer polypeptide of this invention. The admixture is maintained for a predetermined period of time sufficient for the receptor molecules to immunoreact with EBNA present in the body sample. The amount of that immunoreaction is then measured to determine whether EBNA molecules were present or absent in the assayed body sample.

An illustrative diagnostic system in kit form embodying one aspect the present invention that is useful for detecting EBNA present in an aliquot of a body sample contains receptor molecules of this invention such as antibodies, substantially whole antibodies, or antibody combining sites like Fab and F(ab')$_2$ antibody portions raised to a polypeptide of this invention in one package. This system also includes an indicating means for signaling the presence of an immunoreaction between the receptor and the antigen.

Typical indicating means include radioisotopes such as $^{125}$I and $^{131}$I, enzymes such as alkaline phosphatase, horseradish peroxidase, beta-D-galactosidase and glucose oxidase, and fluorochrome dyes such as fluorescein and rhodamine. The indicating means may be linked directly to receptor of this invention. The indicating means may also be linked to a separate molecule such as to a second antibody, to an antibody combining site or to *Staphylococcus aureus* (*S. aureus*) protein A that reacts with (binds to) the receptor of this invention. A specific example of such a separate molecule indicating means is $^{125}$I-labeled *S. aureus* protein A.

The indicating means permits the immunoreaction product to be detected, and is packaged separately from the receptor when not linked directly to a receptor of this invention. When admixed with a body sample such as an acetone-fixed peripheral blood lymphocyte (PBL) smear, the receptor molecule immunoreacts with the EBNA to form an immunoreactant, and the indicating means present then signals the formation of immunoreaction product.

One embodiment of an EBNA diagnostic method is an immunoflourescent assay that includes an amplifying reagent. In such an assay a PBL smear is acetone-fixed to a plain microscope slide. An aliquot of antibodies raised in accordance with this invention, e.g., raised in rabbits, generally about 10 micrograms to about 500 micrograms, is contacted with the slide using well-known techniques.

After rinsing away any un-immunoreacted antibodies of this invention, any non-specific binding sites on the slide are typically blocked with a protein such as bovine serum albumin (BSA), if desired. A second reagent (amplifying reagent) such as complement, or anti-immunoglobulin antibodies, e.g., guinea pig complement, can then be incubated on the test slide.

After this second incubation, any unreacted of the amplifying reagent is removed as by rinsing leaving only that which is bound to the first-named antibodies on the assay slide. A third reagent (indicating means), e.g., antibody, like goat anti-guinea pig complement, is then incubated on the test slide. The third reagent is labeled by being linked to a flourochrome dye such as fluorescein isothiocyanate (FITC), rhodamine B isothiocyanate (RITC), tetramethylrhodamine isothiocyanate (TRITC), 4, 4'-diisothiocyanostilbene-2,2'-disulfonic acid (DIDS), and the like as are well known in the art.

Any unreacted third reagent is rinsed off after this third incubation, leaving any FITC labeled goat-antiguinea pig complement antibodies that bind to the complement on the test slide. The presence of the FITC labeled third reagent may be detected using flourescence microscopy and thereby signal the presence of EBV infection.

B lymphocytes known to be infected with EBV were tested for the presence of EBNA using the immunoflourescence assay method described above and in more detail in the Materials and Methods section II. Rabbit antibodies raised to each of the polypeptides shown in Table 1 were able to detect EBNA in the EBV infected cell line WI-L2.

A preferred diagnostic system, preferably in kit form, useful for carrying out the above assay method includes, in separate packages, (a) receptors (antibodies) of this invention that immunoreact with EBNA, (b) a second, amplifying reagent such as complement, like guinea pig complement, anti-immunogloulin antibodies or *S. aureus* protein A that reacts with the receptor, and (c) an indicating means that may be linked directly to the amplifying means or may be a portion of a separate molecule such as an antibody or antibody-portion that reacts with the amplifying reagent. The indicating means indirectly signals the immunoreaction of the receptor molecule and EBNA through the mediation of the amplifying reagent.

Receptor molecules and separate indicating means of any diagnostic system described herein, as well as the above-described amplifying reagant, may be provided in solution, as a liquid dispersion or as a substantially dry powder, e.g., in lyophilized form. Where the indicating means is a separate molecule from the amplifying reagent, it is preferred that the indicating means be packaged separately. Where the indicating means is an enzyme, the enzyme's substrate may also be provided in a separate package of the system. A solid support such as the before-described microscope slide, one or more buffers and acetone may also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

The use of whole, intact, biologically active antibodies is not necessary in many diagnostic systems such as the immunoflourescent assay described above. Rather, only the immunologically active, idiotype-containing, antigen binding and recognition receptor site; i.e., tne antibody combining site, of the antibody molecule may be used. Examples of such antibody combining sites are those known in the art as Fab and F(ab')$_2$ antibody portions that are prepared by proteolysis using papain and pepsin, respectively, as is well known in the art.

2. Assays For Anti-EBNA Antibodies

Another diagnostic method of this invention is an ELISA that detects anti-EBNA antibodies in a body sample. Here, a particularly preferred polypeptide of this invention such as polypeptide P62 is used as an antigen, and is preferably bound on (adsorbed to) or otherwise linked to a solid matrix such as the cross-linked dextran available under the trademark SEPHADEX from Pharmacia Fine Chemicals (Piscataway, New Jersey), agarose, beads of glass, polyvinyl chloride, polystyrene, cross-linked acrylamide, nitrocellulose or the wells of a microtiter plate to form a solid support.

The particularly preferred polypeptide is admixed with a provided body sample to be assayed. The admixture is maintained for a predetermined time sufficient for anti-EBNA antibodies present in the body sample to immunoreact with the polypeptide. The presence of that immunoreaction is then determined as with an indicting means to signal the presence of anti-EBNA antibodies in the assayed body sample.

An exemplary ELISA utilizing the above method uses a solid support comprised of a particularly preferred polypeptide of this invention adsorbed onto a solid matrix comprised of the wells of a twelve or ninety-six well microtiter plate made of polystyrene or polyvinyl chloride. Non-specific binding sites on the microtiter well walls are thereafter typically blocked with a protein such as bovine serum albumin (BSA). Unbound polypeptide and BSA are removed from the microtiter well as by rinsing.

A body sample aliquot such as human serum, blood or plasma is admixed with the above-described polypeptide-bound solid support to form an admixture containing solid and liquid phases. The solid-liquid phase admixture is maintained for a time sufficient for anti-EBNA antibodies in the body sample to immunoreact with the polypeptide antigen. The solid and liquid phases are thereafter generally separated.

A solution of a second, labeled, indicating means-containing antibody, antibody combining site or S. aureus protein A that reacts with the first-named antibody is then admixed with the solid phase to form another solid-liquid phase admixture. An exemplary second antibody is a peroxidase-labeled goat anti-human Ig antibody where the first-named antibodies are from a human body sample. Additional, useful enzyme labels include alkaline phosphase, beta-D-galactosidase and glucose oxidase. The admixture formed from the solid phase and the second labeled antibody solution is maintained (incubated) for a predetermined time period (e.g., 30 minutes) sufficient to form a reactant between the first-named antibody and the indicating means such as an immunoreaction between the two antibodies. The solid and liquid phases are thereafter separated.

The second antibody described above may also be specific for and immunoreact with only one of the classes of immunoglobulin (e.g., IgG, IgM, IgE, IgA, or IgD). Such antibodies provide the ability to identify the immunoglobulin class of anti-EBNA antibody present in the body sample, as is shown in Table 6, hereinafter. In addition, the second antibody or antibody combining site may be specific for and immunoreact with only one of the two types of immunoglobulin light chains (e.g., kappa or lambda). These antibodies provide the ability to identify the isotype of the immunoglobulin molecule present in the body sample.

A solution containing a substrate for the enzyme label such as hydrogen peroxide for peroxidase and a color-forming dye precursor such as o-phenylenediamine, or p-nitrophenyl phosphate for alkaline phosphatase is thereafter admixed with the solid phase. The optical density at a preselected wavelength (e.g., 490 or 405 nanometers, respectively) may then be determined after a predetermined time period has elapsed (e.g., 60 minutes), and compared to the optical density of a control to determine whether anti-EBNA antibodies were present in the body sample.

Another embodiment of this invention comprises a diagnostic system in kit form that includes a solid support comprised of a solid matrix such as a polystyrene twelve-well microtiter strip, and a polypeptide of this invention, absorbed (bound) or otherwise affixed to the solid matrix to form a solid matrix. This system preferably also includes separately packaged anti-human Ig antibodies having a linked indicating means such as peroxidase-labeled goat anti-human Ig antibodies, and may also include substrate for the linked indicating means such as hydrogen peroxide and a color forming due precursor such as o-phenylenediamine, in further, separate packages. Hydrogen peroxide is typically not included in the kit due to its relative instability, and is typically supplied by the end user. Buffer salts useful in an assay utilizing this system may also be included in one or more separate packages in dry or liquid form. Separate packages containing human anti-EBNA antibodies and human antibodies free from anti-EBNA antibodies (normal human antibodies) may also be included as positive and negative controls, respectively. An assay for the presence of anti-EBNA antibodies in a body sample such as serum may be carried out with this diagnostic system using the above-described method.

An exemplary ELISA, similar to that described before and described in detail in the Materials and Methods section (II) hereinafter, was used to screen for the presence of anti-polypeptide immunoglobulin in the sera of 91 people with anti-EBNA positive serotypes established using the anti-complement immunofluorescence (ACIF) described hereinbefore. When the sera were assayed at a 1:20 dilution, all 91 were positive against (bound to) polypeptides P27, P62, P60 and F16, F14 and F15. Even at the higher dilution of 1:320, 83 of the 91 EBNA positive sera immunoreacted with polypeptide P62 in the ELISA. Thus, there appears to be an excellent correlation between the anti-EBNA antibody titer establisned by ACIF and tne antipeptide activity of each serum.

In addition, the results illustrate an excellent correlation between the ACIF method and the present ELISA technique, which is simpler and easier to use. Still further, the results illustrate the usefulness of polypeptides of this invention for a diagnostic assay for anti-EBNA antibodies.

Table 5, below, shows the reactivities of sera obtained from two subjects before and after contracting EBV-induced infectious mononucleosis (IM). In both cases antibodies that bind to polypeptides P27, P62 and P60 were absent before infection, but appeared afterward. In contrast, no antibodies were produced by either of these individuals that bound to polypeptide P89.

In further study, stored sera from a previously reported panel of 27 EBV non-immune donors [Catalano et. al., *J. Clin. Invest.*, 65:1238-1245 (1980)] were screened for binding to polypeptides P62 and P60 in the before-described ELISA. The EBV-immune status of the sera used was defined by the presence or absence of Epstein-Barr viral capsid antigen (VCA). Individuals who have no serum antibodies to VCA (VCA−) have never been infected with EBV. VCA positive (VCA+) individuals have had EBV infections and typically carry a low level of anti-EBNA antibodies. None of tne sera displayed significant reactivity to either polypeptide as is seen from Table 5, below.

TABLE 5

ANTIBODIES TO EBNA PEPTIDES IN HUMAN SERA[1]

| PATIENT | OD$_{405}$ × 10$^3$ obtained[2] with Patient Antibodies to: | | | |
|---|---|---|---|---|
| | P27 | P62 | P60 | P89 |
| VCA+ Normal 1[3] | 155 | 958 | 154 | 23 |
| VCA+ Normal 2[3] | 516 | 819 | 145 | 16 |
| SB pre-mononucleosis | 11 | 13 | 51 | 9 |
| SB post-mononucleosis | 33 | 514 | 115 | 23 |
| MV pre-mononucleosis | 15 | 77 | 72 | 29 |
| MV post-mononucleosis | 107 | 631 | 162 | 25 |
| VCA-Normals (n = 27)[4] | 67 ± 23[5] | ND[6] | 45 ± 18 | ND |

[1]All sera were tested at a dilution of 1:20.
[2]Optical density measured at 405 nanometer light wavelength after 30 minute substrate incubations.
[3]VCA+ sera from individuals showing no clinical signs of present EBV related disease.
[4]Sera from 27 individuals showing no clinical signs of EBV related disease, past or present, as indicated by the absence of antibodies to VCA.
[5]Average optical density ± one standard deviation.
[6]Not done.

To examine the correlation between the ELISA and the ACIF diagnostic technique through the course of infection, stored sera from 8 college-age students, collected sequentially after onset of infectious mononucleosis (IM), were examined in the before-described ELISA using polypeptide P62. All students developed anti-EBNA titers from 1 month to 1 year following infection as measured by the classical method; i.e., ACIF. Henle, et. al., *J. Infect. Dis.*, 130:231-239, (1974).

In one-half of the subjects, anti-P62 antibodies rose in parallel with the corresponding anti-EBNA titer as is shown for patient 15 in FIG. 4. In the other half, antibodies against polypeptide P62 were detected in the first month after the onset of symptoms while those antibodies were detected at later times using the ACIF technique. These results are shown for patients 14 and 2 in FIG. 5. Anti-P62 antibodies were therefore detectable using the ELISA of the present invention before anti-EBNA antibodies were detectable by the standard anti-complement immunoflourescence assay.

To differentiate the class of immunoglobulin predominantly responsible for an individual's immune response at a given time during the course of infectious mononucleosis (IM), secondary (indicating) antibodies specific for human IgG or IgM were used in the ELISA as described in the Methods and Materials section (II). Table 6, below, shows the results of this study with the sera of two individuals from different points in time during EBV infection measured against polypeptide P62 in the ELISA.

TABLE 6

POLYPEPTIDE P62-BOUND ELISA-DETECTED APPEARANCE OF ANTIPEPTIDE ACTIVITY AFTER MONONUCLEOSIS INFECTION

| Time After Infection | Patient MV | | Patient 15 | |
|---|---|---|---|---|
| | IgM[1] | IgG[2] | IgM[1] | IgG[2] |
| Pre Infection | 103[3] | 74 | ND[4] | ND |
| 1 Week | 245 | 80 | 152 | 113 |
| 1 Month | 87 | 37 | 225 | 118 |
| 3 Months | 136 | 60 | 208 | 118 |
| 12 Months | ND | ND | 249 | 375 |
| 21 Months | 145 | 600 | 185 | 994 |

[1]Patient IgM level detected using a second antibody specific for human IgM.
[2]Patient IgG level detected using a second antibody specific for human IgG.
[3]Optical density measured at 405 nanometer light wavelength.
[4]Not done.

Using this ELISA method, the rise in IgM antibody values, although small, are repeatable and found in all sequential sera tested. The immune response measured by the ELISA assay is normal in that IgM classically appears before IgG during EBV infection. The appearance of IgM antibodies prior to IgG antibodies is particularly well shown for patient 15 in Table 6. The above results again show that infection with EBV causes the production of antibodies that react with at least one polypeptide of this invention.

In a larger anti-polypeptide ELISA study, the panel of 19 VCA− sera described hereinbefore were screened against polypeptides P27, P62, P60, F12, F13, F14, F15 and F16. None of the VCA− sera were found to react positively. Typical data are shown in Table 7, below. Sera From clinically normal individuals positive for VCA antibodies were tested at two dilutions. Typical results, shown in Table 7 below, indicate that all of the VCA+ indiviuals were positive for; i.e., had antibodies that bound to, each of the polypeptides.

The sera of a number of rheumatoid arthritis (RA) patients were also screened in the ELISA. These results are also summarized in Table 7.

TABLE 7

ELISA-DETERMINED AVERAGE ANTIPEPTIDE LEVELS IN HUMAN SERA

| Patient Group | Number of Sera | Average Antibody Activity to Polypeptides[1] | | | | | |
|---|---|---|---|---|---|---|---|
| | | P27 | P62 | P60 | F12 | F13 | F16 |
| Nor−[2] | 1/20[3] | 19 | 22 | 17 | 77 | 34 | 41 | 47 |
| Nor+[4] | 1/20 | 26 | 521 | 854 | 394 | 128 | 70 | 733 |
| Nor+ | 1/320 | 48 | 90 | 223 | 70 | 37 | 37 | 166 |
| RA+[5] | 1/20 | 28 | 597 | 999 | 564 | 118 | 113 | 843 |
| RA+ | 1/320 | 48 | 126 | 348 | 122 | 50 | 50 | 231 |

[1]Activity measured as optical density at 405 nanometers light wavelength after 30 minutes of serum incubation.
[2]VCA negative individuals.
[3]Dilution at which sera were tested.
[4]VCA positive individuals.
[5]Individuals diagnosed as having rheumatoid arthritis.

The difference between the normal, VCA positive (control) and RA patients can best be seen at the serum dilution 1:320. The antibody levels in RA patients were significantly higher for every polypeptide tested at this dilution when analyzed using the Wilcox Rank Sum method (significance level greater than 99%).

Patients with Sjogren's Syndrome, Systemic Lupus Erythematosus (SLE) and Progressive Systemic Schlerosis (PSS) were also screened at both high and low serum dilutions. The only differences found between these patient groups and normals was a relatively higher average titer of the PSS patients to polypeptides P27, P62, P60, F16, F14 and F15. These results are believed to possibly be due to a previous EBV related infection or the involvement of EBV in those autoimmune diseases. These data do not detract from the usefulness of the ELISA as a diagnostic method.

3. Preparation For Passive Immunization

A patient with latently infected B lymphocytes that express EBNA on their cell surfaces can be treated with receptors of this invention, preferably as whole antibodies, raised to the synthetic polypeptides of the present invention that immunoreact with EBNA. The receptors are administered in a unit dose having an effective amount of receptors dispersed in a pharmaceutically acceptable diluent.

An effective amount of such antibodies varies depending on the reactivity and type of the antibodies. Generally, about 0.5 milligrams to about 25.0 milligrams of antibody per kilogram patient body weight is considered effective. The antibodies can be administered intravenously, intramuscularly, or intraperitoneally, with several administrations given at 3 to 20 day intervals. The antibodies can also be given in conjunction with surgical or chemical treatment.

The antibodies can be obtained from the sera or plasma of an animal species different from tne patient to be treated by raising antibodies to the polypeptide of this invention using the before-described inocula. The antibodies can also be obtained from monoclonal sources such as ascites fluid by preparing a hybridoma cell line using techniques known in the art. Whole antibodies are preferred as the combining site since they are capable of activating the complement system when an immune complex is formed.

II. METHODS AND MATERIALS

A. Synthesis of Polypeptides

The polypeptides of this invention were chemically synthesized by solid-phase methods as described in Merrifield et. al., *J. Am. Chem. Soc.*, 85:2149-2154 (1963) and Houghten et. al., *Int. J. Pept. Prot. Res.* 16:311-320 (1980). The solid phase method of polypeptide synthesis was practiced utilizing a Beckman Model 990B Polypeptide Synthesizer, available commercially from Beckman Instrument Co., Berkeley, Calif., U.S.A.

For polypeptides having fewer than 35 residues that were used in inocula, a cysteine residue was added to the amino-terminus or to the carboxyl-terminus to assist in coupling to a protein carrier as described below. The compositions of all polypeptides were confirmed by amino acid analysis.

In preparing a synthetic polypeptide of this invention by the above solid phase method, the amino acid residues are linked to a resin (solid phase) through an ester linkage from the carboxy-terminal residue. When the polypeptide is to be linked to a carrier via a Cys residue or polymerized via terminal Cys residues, it is convenient to utilize that Cys residue as the carboxy-terminal residue that is ester-bonded to the resin.

The alpha-amino group of each added amino acid is typically protected by a tertiary-butoxycarbonyl (t-BOC) group prior to the amino acid being added into the growing polypeptide chain. The t-BOC group is then removed prior to addition of the next amino acid to the growing polypeptide chain.

Reactive amino acid side chains were also protected during synthesis of the polypeptides. Usual side-chain protecting groups were used for the remaining amino acid residues as follows: O-(p-bromobenzyloxycarbonyl) for tyrosine; O-benzyl for threonine, serine, aspartic acid and glutamic acid; S-methoxybenzyl for cysteine, dinitrophenyl for histidine; 2-chlorobenzoxycarbonyl for lysine and tosyl for arqinine.

Protected amino acids were recrystallized from appropriate solvents to give single spots by thin layer chromatoqraphy. Couplings were typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.* 58:248-249 (1972).

After preparation of a desired polypeptide, a portion of the resulting, protected polypeptide (about 1 gram) was treated with two milliliters of anisole, and anhydrous hydrogen flouride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen flouride at a temperature of 4 degrees C. with a stream of $N_2$, the residue was extracted with anhydrous diethyl ether three times to remove the anisole, and the residue was dried in vacuo.

Tne vacuum dried material was extracted with 5% aqueous acetic acid (3 times 50 milliliters) to separate the free polypeptide from the resin. The extract-containing solution was lyophilized to provide a monomeric unoxidized polypeptide.

The produced synthetic polypeptide may be used as a reagent in an exzyme-linked immunosorbent assay (ELISA) to detect anti-EBNA antibodies. The synthetic polypeptide may also be used to produce an inoculum, usually by linking it to a carrier to form conjugate and then dispersing an effective amount of the conjugate in a physiologically tolerable diluent, as is discussed hereinafter.

It is also to be noted that a synthetic multimer of this invention can be prepared by the solid phase synthesis of a plurality of the polypeptides of this invention linked together end-to-end (head-to-tail) by an amide bond between the carboxyl-terminal residue of one polypeptide and the amino-terminal residue of a second polypeptide. Such synthetic multimers are preferably synthesized as a single long polypeptide multimer, but can also be prepared as individual polypeptides that are linked together subsequent to their individual syntheses, using a carbodiimide reagent such as 1-(3-dimethylaminopropyl)-3-ethylcarbodiimide hydrochloride in water. The total number of amino acid residues contained in a multimer prepared as a single polypeptide chain is preferably less than about 50, so that up to about eight polypeptides of this invention can be incorporated into a single head-to-tail multimer chain that is synthesized as a single polypeptide. A synthetic head-to-tail multimer more preferably contains two to about four blocks of linked, synthetic, random copolymer polypeptides of this invention, and a total of less than about 40 amino acid residues.

B. Preparation of Polymers

The polypeptides of the present invention may be connected together to form an antigenic and/or immunogenic polymer (synthetic multimer) comprising a plurality of the polypeptide repeating units. Such a polymer typically has the advantage of increased immunogenicity and antigenicity. In addition, a carrier is typically not needed when a polymeric immunogen is utilized. Where different polypeptide monomers are used to make up the polymer, the ability to immunoreact with antibodies to several EBNA antigenic determinants is obtained. A still further advantage is the ability of such a polymer wnen used in an inoculum to induce antibodies that immunoreact with several antigenic determinants of EBNA.

A polymer of this invention may be prepared by synthesizing the polypeptides as discussed above and including cysteine residues at both the amino and carboxy-termini to form a "diCys-terminated" polypeptide. For example, each of the polypeptides of Table 1 and polypeptides D1 and D2 of Table 2 may be synthesized to contain an additional Cys residue at each of the amino- and carboxy-termini to provide diCys-terminated polypeptides in their reduced forms. After synthesis, in a typical laboratory preparation, 10 milligrams of the diCys polypeptide (containing cysteine residues in un-oxidized form) are dissolved in 250 milliliters (ml) of 0.1 molar (M) ammonium bicarbonate buffer. The dissolved diCys-terminated polypeptide is then air oxidized by stirring the resulting solution gently for a period of about 18 hours in the air, or until there is no detectable free mercaptan by the Ellman test. [See Ellman, *Arch. Biochem. Biophys.*, 82:70–77 (1959).]

The polymer (synthetic multimer) so prepared contains a plurality of the synthetic, random copolymer polypeptide repeating units that are bonded together by oxidizing cysteine (cystine) residues. Such polymers typically contain their polypeptide repeating units bonded together in a head-to-tail manner as well as in head-to-head and tail-to-tail manners; i.e., the amino-termini of two polypeptide repeating units may be bonded together through a single cystine residue as may two carboxyl-termini since tne linking groups at both polypeptide termini are identical.

C. Coupling To Carriers

The synthetic polypeptides were coupled to keyhole limpet hemocyanin (KLH) as carrier by the method described in Liu et al., *Biochem.*, 80:690 (1979). Briefly, 4 milligrams (mg) of the carrier were activated with 0.51 mg of m-maleimidobenzoyl-N-hydroxysuccinimide ester, and were subsequently reacted with 5 mg of the polypeptide through an amino- or carboxy-terminal cysteine to provide a conjugate containing about 10 to about 35 percent by weight polypeptide.

One or more additional amino acid residues may be added to the amino- or carboxy- termini of the synthetic polypeptide to assist in binding the polypeptide to a carrier. As discussed before, cysteine residues added at the amino- or carboxy-termini of the synthetic polypeptide have been found to be particularly useful for forming polymers via disulfide bonds. However, other methods well known in the art for preparing conjugates can also be used. Exemplary additional linking procedures include the use of Michael addition reaction products, dialdehydes such as glutaraldehyde, Klipstein et al., *J.Infect. Dis.*, 147:318-326 (1983) and the like, or the use of carbodiimide technology as in the use of a water-soluble carbodiimide to form amide links to the carrier, as discussed before for linking a plurality of polypeptides together to form a synthetic multimer.

Useful carriers are well known in the art, and are generally proteins themselves. Exemplary of such carriers are keyhole hemocyanin (KLH), edestin, thyroglobulin, albumins such as bovine serum albumin (BSA) or human serum albumin (HSA), red blood cells such as sheep erthrocytes (SRBC), tetanus toxoid, cholera toxoid as well as polyamino acids such as poly (D-lysine:D-glutamic acid), and the like.

As is also well known in the art, it is often benefical to bind a synthetic polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS), as was used herein.

Additionally, MBS may be first added to the carrier by an ester-amide interchange reaction as disclosed by Liu et al., supra. Thereafter, the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate use of the immunogen than upon the determinant portion of the immunogen, and is based upon criteria not particularly involved in the present invention. For example, if a inoculum is to be used in animals, a carrier that does not generate an untoward reaction in the particular animal should be selected.

D. ELISA

Anti-peptide antibody binding and inhibition studies were carried out by an enzyme-linked immunosorbent assay (ELISA) as described below.

Briefly, microtiter wells (Costar, #3590, Cambridge, Mass.) were coated with individual polypeptides as antigens by adding 100 microliters (ul) of BBS [10 millimoler (mM) sodium borate (pH 8.3), 150 mM NaCl] containing polypeptide at a concentration of 10 micrograms per milliliter (ug/ml). Contact between the wells and antigen-containing solution was maintained for a predetermined time, typically 15 minutes, and at 20 degrees C., to form an antigen-coated solid phase. The solid and liquid phases were separated and the wells were washed three times with BBS.

Non-specific binding sites were blocked by admixing 200 microliters of 1% bovine serum albumin (BSA) in each well to form another solid-liquid phase admixture, and maintaining that solid-liquid phase admixture for 30 minutes, at 20 degrees C. The phases were separated and excess, unbound BSA was removed by washinq three times with BBS.

Rabbit and human sera (body sample aliquots) were assayed for anti-polypeptide activity by adding 100 microliters of a serum diluted 1:20 in BBS per well to form a solid/liquid phase composition. Contact between the diluted sera and the antigen-coated solid phase was maintained for a predetermined time such as 1 hour, and at 20 degrees C., for an immunoreactant to form. The solid and liquid phases were separated, and the solid phase; i.e., antigen-coated, immunoreactant-containing wells, was then washed three times with BBS.

The antibodies in human sera that immunoreacted with an adsored polypeptide were detected using an indicating means comprising alkaline phosphatase-conjugated goat anti-human Ig antibody (Tago, Burlington, CA). The antibodies in rabbit sera that immunoreacted with an adsorbed polypeptide were detected using an indicating means comprising alkaline phosphatase-conjugated goat anti-rabbit Ig antibody (Kirkegard & Perry Laboratories, Inc., Gaithersburg, Md.). In either instance, 100 microliters of the indicating antibody diluted 1:300 in BBS were added per well to form a further solid-liquid phase composition. This solidliquid phase composition was maintained for a predetermined time, one hour, for the formation of a reaction product between the human antibodies bound to the solid phase and the indicating means, and at 20 degrees C. The phases were separated, and the solid phase was washed 3 times with BBS.

Alkaline phosphatase-conjugated antibody bound to polypeptide specific antibody was detected by spectrophotometrically measuring the enzymatic hydrolysis of p-nitrophenyl phosphate to p-nitrophenol. Briefly, 100 microliters of p-nitrophenyl phosphate [1 milligram per milliliter in 2 mM MgCl 2, (pH 9.8), 50 mM sodium carbonate] were added to each well. The enzymatic reaction was allowed to proceed 1 hour and then the optical density at 405 nm was determined in a TITER-TEK spectrophotometer available from Flow Laboratories, Inglewood, Calif.

E. Cell Culture

The ability of the receptor molecules of this invention to immunoreact with EBNA produced in cells was studied as described hereinabove using the WI-L2, Raji, Daudi and BJAB cell lines. WI-L2 cells (ATCC CRL 8155 W1L2-NS, American Type Culture Collection, Bethesda, Md.) are an EBV genome-positive non-producer B-lymphoblast line, derived from a human patient with hereditary spherocytic anemia. Levy, et al., *Cancer* 22:517-524 (1968).

Raji cells (ATCC CCL 86, Americal Type Culture Collection, Bethesda, Md.) are an EBV genome-positive, EBNA procuding lymphoblast-like cell line from a Burkitt lymphoma. Epstein, *J. Nat. Cancer Inst.* 34: 231 (1965). Daudi cells (ATCC CCL 213, American Type Culture Collection, Bethesda, Md.) are also an EBNA producing cell line. BJAB cells are a non-EBNA producing lymphocyte cell line available at the Scripps Clinic and Research Foundation, La Jolla, Calif.

The above cell lines were cultured in RPMI 1640 medium [Moore, *J. Am. Med. Assoc.* 199:519-524 (1967); and Morton, *In Vitro* 6:89-100 (1970)] supplemented with 2 mM L-glutamine and 10% fetal calf serum.

F. Whole Cell Extracts

Extracts of EBNA producing and non-producing (control) cells were prepared to determine if receptor molecules of this invention were useful for diagnosing EBNA expression. Cells from cultures described hereinabove were washed in phosphate-buffered saline (PBS; 150 mM NaCl, 10 mM sodium phosphate, pH 7.4) containing 0.2 mM phenylmethylsulfonyl fluoride, swollen for 5 minutes in reticulocyte standard buffer (RSB; 10 mM NaCl, 10 mM Tris-HCl, pH 7.4, 1.5 mM MgCl$_2$, 0.2 mM phenylmethylsulfonyl fluoride, and lysed by sonication in 3-5 volumes of RBS adjusted to 0.2-0.35 molar (M) NaCl. After 30 minutes on ice, the sonicate was centrifuged at 10,000×g for 15 minutes to remove cellular debris.

G. Immunoblotting Procedures

Cell extracts obtained above were assayed for EBNA using human sera known to contain anti-EBNA antibodies or exemplary receptor molecules of this invention. Tne extracts were either concentrated by precipitation with 2 volumes of ethanol at −20 degrees C. for about 18 hours, and were then dissolved in sample buffer [SB; 10% glycerol, 2% 2-mercaptoethanol, 1% sodium dodecyl sulfate (SDS), 0.002% bromphenol blue, 40 mM Tris-HCl (pH 7.4)] or diluted 1:6 in sample buffer for SDS-polyacrylamide gel electrophoresis (SDS-PAGE). 7.5% Polyacrylamide gels were cast and run according to the procedure of Laemmli, *Nature*, 277:680-685 (1970), applying 50 to 200 micorgrams of total protein per lane.

After electrophoresis, the protein bands from the SDS polyacrylamide gels were transferred electrophoretically to a solid support in the form of nitrocellulose sheets (Schleicher and Schuell, Detroit, Mich.) by the procedure of Towbin et al., *Proc. Natl. Acad. Sci., U.S.A.*, 76:4350-5354 (1979). This was accomplished using a Bio-Rad Trans-Blot apparatus (Bio-Rad, Richmond, Calif.) at 70 volts for 2-3 hours in 12.5 mM Tris hydroxide, 96 mM glycine and 20% methanol.

Following transfer, the nitrocellulose filters or blots were saturated for one hour in either 2% BSA (w/v) in PBS or 2% powdered milk (w/v) in PBS to reduce non-specific . binding. The blots were than immunoreacted with 0.1 ml of either EBNA positive human serum or rabbit anti-polypeptide antibodies in 2 ml of PBS or 2% milk for 1 hour at 37 degrees C.

Anti-peptide antibodies bound to EBNA protein were detected by reacting the blots with an indicating means. In this instance, 20 ml of $^{125}$I-labeled [200,000 counts per minute per milliliter (cpm/ml), $10^6$ counts per minute per milligram (cpm/mg)] *S. aureus* protein A (Calbiochem, La Jolla, Calif.) were contacted with the immunoreaction product for 30 minutes at 37 degrees C. The blots were washed with PBS and exposed to Kodak XAR X-ray film overnight at −70 degrees C.

H. Immunizations

The receptor molecules of this invention include whole antibodies raised in mammals by immunizing them with inocula including a polypeptide and/or multimer as described hereinabove. Both polypeptides and multimers may be used included in inocula alone or conjugated to a carrier protein such as keyhole limpet hemocyamin (KLH). However, polypeptides are preferably used as a conjugate and multimers are preferably used alone.

Rabbits were immunized with inocula containing 1.0 mg of conjugate in complete Freund's adjuvant (CFA), and boosted one month later with 1.0 mg of conjugate in incomplete Freund's adjuvant (IFA). Each immunization consisted of one subcutaneous injection, on the back hip. Rabbits were bled 1 and 2 months subsequent to the boost.

Sera containing immunologically active antibodies were then produced from the bleeds by methods well known in the art. These antibodies immunoreacted with one or more of the polypeptides of this invention, and an EBNA antigenic determinant. They may thus be used in a system to assay EBNA.

Individual inocula were prepared with CFA or IFA as follows: An amount of conjugate sufficient to provide the desired amount of polypeptide per inoculation (e.g., 1 mg) was dissolved in PBS (at about 0.5 ml) at pH 7.2. Equal volumes of CFA or IFA were then mixed with the conjugate solutions to provide an inoculum containing conjugate, water and adjuvant in which the water to oil ratio was 1:1. The mixture was thereafter homogenized to provide the inocula. The volume of an inoculum so prepared was typically greater than 1 ml, and some of the conjugate, PBS and adjuvant was lost during the emulsification. Substantially all of the emulsion that could be recovered was placed into a syringe, and then was introduced into the rabbits as discussed before. The amount of inoculum introduced into the rabbits is believed to have been about 90 percent of that present prior to the emulsification step.

The above inocula stock solutions are illustrative of the inocula of this invention. As demonstrated herein, they may be used to produce receptor molecules that immunoreact with EBNA.

I. Immunofluorescense Procedures

Another illustrative method for assaying EBNA in a body sample uses receptor molecules of this invention and a fluorochromatic indicating means to detect the product of a receptor-EBNA immunoreaction.

In the present study, $2 \times 10^4$ WI-L2 cells, grown as described above, were spread on a plain microscope slide using a cytocentrifuge (CYTOSPIN, Shandon Southern, Astmoor, Runcorn, Chesire, England). After air drying for 5 minutes at 20° C., the cells were fixed in acetone for 2 minutes, then air dried for 2 minutes at 20° C. The slides were stored at $-20°$ C. until used.

The fixed WI-L2 cells were assayed for EBNA using rabbit anti-polypeptide antibodies (receptors of this invention) raised to polypeptides P27, P60, P62 and P89. Fifty ul of each rabbit antiserum, diluted 1:10 in VBS buffer (120 mM barbitol pH 7.3, 144 mM NaCl, 2.5 mM MgCl$_2$ and 0.75 mMCaCl$_2$) were incubated (contacted and maintained in contact with the fixed cells) at 20° C. on a slide for a predetermined period of time (e.g. 30 minutes) sufficient for the antibodies and EBNA to immunoreact. A negative control slide was treated in identical manner with normal rabbit serum.

During the above incubation, a portion of tne antipolypeptide antibodies immunoreacted with EBNA present in the fixed WI-L2 cells. Unbound antibodies were removed by washing with VBS, leaving only the EBNA-receptor immunoreaction product on the slide.

Anti-polypeptide antibodies bound to EBNA were detected by first incubating 50 ul of guinea pig complement (Tago, Burlingame, CA) diluted 1:10 in VBS on each slide for a period of time (30 minutes) sufficient for the complement to bind to the receptors. The slides were then washed with VBS to remove any complement not bound to the rabbit anti-polypeptide IgG.

Fluorescein labeled goat anti-guinea pig C$_3$ (labeled anti-complement antibodies, Cappel Laboratories, Cochranville, Pa.) was used to detect the antigen-antibody-complement complexes. Fifty ul of the indicating antiserum, diluted 1:20 in VBS, were incubated as above on each slide for 30 minutes at 20° C. Unbound goat anti-guinea pig C$_3$ was washed off the slide with VBS. Immunoreaction products were then visualized by fluorescent microscopy.

J Circular Dichroism Spectroscopy

Figure 1:
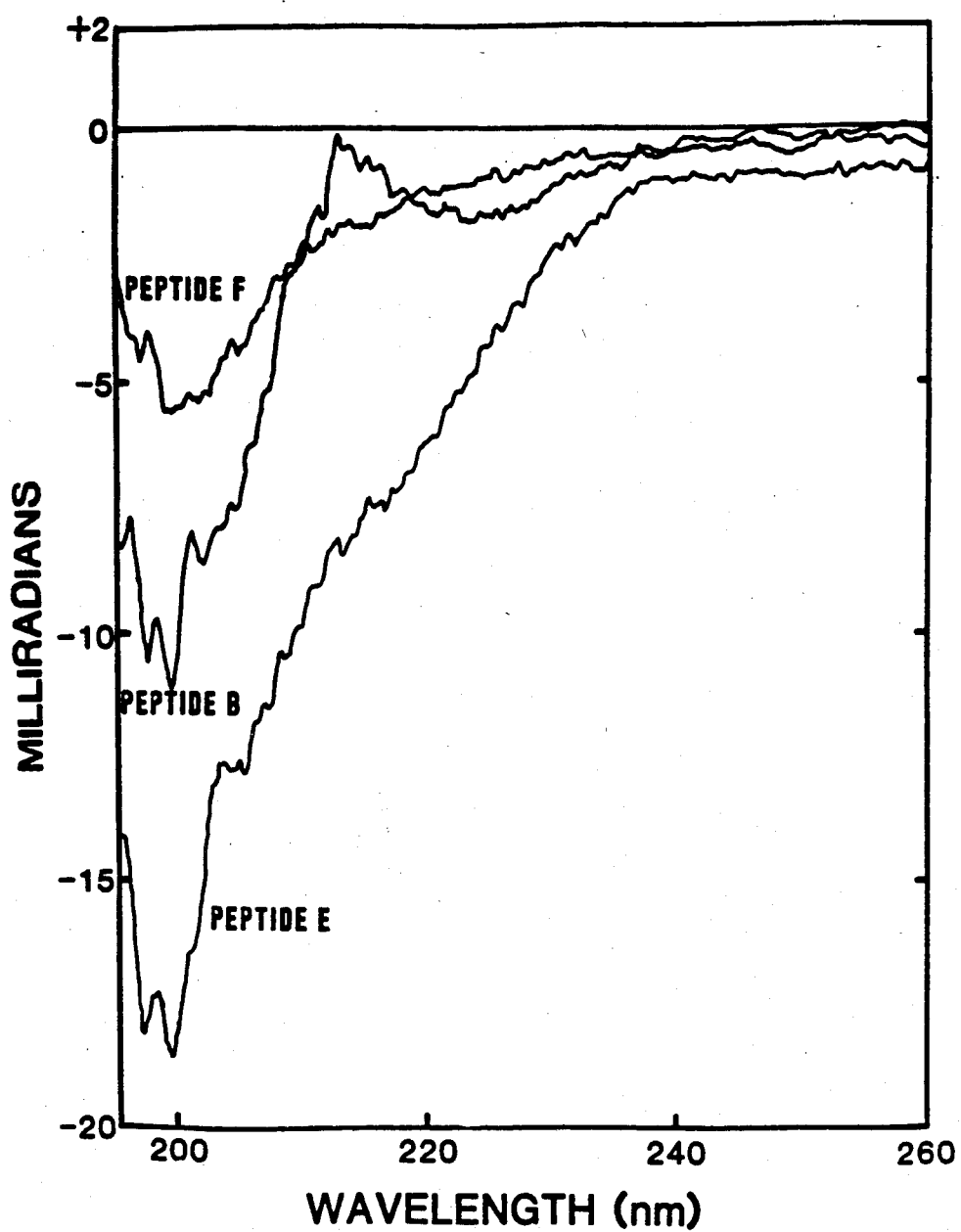
FIG. 1 is a plot of the circular dichroism spectra of polypeptides (F), (B) and (E). These polypeptides are also referred to herein as polypeptides F13, F62 and F12, respectively. Each spectrum is the average of 10 successive scans of a polypeptide in pnysiological solution (phosphate buffered saline) at a concentration of 1 milligram/milliliter (mg/ml). The optical rotation is expressed as milliradians and is plotted against the polarized light wavelength, expressed in nanometers (nm). The relatively featureless plot for polypeptide F (F13) is indicative of a random conformation that is the usual result obtained with peptides of this size. The trough and peaks spectrum demonstrated by polypeptide B (P62) is characteristic of a relatively stable secondary structure or conformation, probably beta-pleat. Although the data are not shown, the polypeptides P27, P60, F14 and F15 have very similar spectra indicating that the more preferred polypeptides of this invention exist as similar stable conformations in physiological solution. The spectrum of polypeptide E (F12) indicates partial assumption of such conformation.

The conformational properties of the polypeptides were investigated to elucidate any secondary structure that might be necessary for polypeptide immunoreaction with human anti-EBNA antibodies. The polypeptides were dissolved at a concentration of 1 mg/ml in phosphate-buffered saline (PBS). Spectra were taken using 1 ml samples in a Cary 61 spectropolarimeter (Cary Instruments, Applied Physics Corp., Monrovia, Calif.) interfaced and automated with a Digital Equipment Corporation 11/02 computer (Digital Equipment Corporation, Maynard, Mass.). The average of 10 successive scans for each polypeptide was plotted as shown in FIG. 1.

The foregoing is intended as illustrative of the present invention but not limiting. Numerous variations and modifications may be effected without departing from the true spirit and scope of the novel concepts of the invention. It is to be understood that no limitation with respect to the specific polypeptides, antibodies, their compositions and uses illustrated herein is intended or should be inferred.

What is claimed is:

1. A synthetic polypeptide having an amino acid residue sequence, taken from left to right and in the direction of amino-terminus to carboxy-terminus, represented by the formula:

H-Arg-Ala-Arg-Gly-Arg-Gly-Arg-Gly-Arg-Gly-Glu-Lys-Arg-Pro-Met-OH;

the pharmaceutically acceptable salts thereof, and antigenically related variants thereof.

2. A synthetic polypeptide having an amino acid residue sequence, taken from left to right and in the direction of amino-terminus to carboxy-terminus, represented by the formula:

H-Ile-Met-Ser-Asp-Glu-Gly-Pro-Gly-Thr-Gly-Asn-Gly-Leu-Gly-Glu-OH;

the pharmaceutically acceptable salts thereof, and antigenically related variants thereof.

3. A synthetic polypeptide having an amino acid residue sequence, taken from left to right and in the direction of amino-terminus to carboxy-terminus, represented by the formula:

H-Pro-Gly-Ala-Pro-Gly-Gly-Ser-Gly-Ser-Gly-Pro-OH;

the pharmaceutically acceptable salts thereof, and antigenically related variants thereof.

4. A synthetic polypeptide having an amino acid residue sequence, taken from left to right and in the direction of the amino-terminus to carboxy-terminus, represented by the formula:

H-Gly-Gly-Gly-Ala-Gly-Ala-Gly-Gly-Ala-Gly-Ala-Gly-Gly-Gly-Gly-Arg-OH;

the pharmaceutically acceptable salts thereof, and antigenically related variants thereof.

5. A synthetic polypeptide having an amino acid residue sequence, taken from left to right and in the direction of amino-terminus to carboxy-terminus, represented by the formula:

H-Lys-Gly-Thr-His-Gly-Gly-Thr-Gly-Ala-Gly-Ala-Gly-Ala-Gly-Gly-Ala-Gly-Ala-Gly-OH;

the pharmaceutically acceptable salts thereof, and antigenically related variants thereof.

6. A synthetic polypeptide having an amino acid residue sequence, taken from left to right and in the direction of amino-terminus to carboxy-terminus, represented by the formula:

H-Gly-Gly-Gly-Ala-Gly-Gly-Ala-Gly-Ala-Gly-Gly-Gly-Ala-Gly-Gly-Ala-Gly-OH;

the pharmaceutically acceptable salts thereof, and antigencally related variants thereof.

7. A synthetic polypeptide having an amino acid residue sequence, taken from left to right and in the direction of amino-terminus to carboxy-terminus, represented by the formula:

H-Gly-Gly-Ala-Gly-Gly-Ala-Gly-Gly-Ala-Gly-Ala-Gly-Gly-Ala-Gly-OH;

the pharmaceutically acceptable salts thereof, and antigenically related variants thereof.

8. A synthetic polypeptide having an amino acid residue sequence, taken from left to right and in the direction of amino-terminus to carboxy-terminus, represented by the formula:

H-Gly-Gly-Ala-Gly-Ala-Gly-Gly-Ala-Gly-Ala-Gly-Gly-Ala-Gly-Ala-Gly-Gly-Ala-Gly-Ala-Gly-OH;

the pharmaceutically acceptacle salts thereof, and antigenically related variants thereof.

9. A synthetic polypeptide having an amino acid residue sequence, taken from left to right and in the direction of amino-terminus to carboxy-terminus, represented by the formula:

H-Gly-Ala-Gly-Gly-Ala-Gly-Ala-Gly-Gly-Ala-Gly-Gly-Ala-Gly-Gly-OH;

the pharmaceutically acceptable salts thereof, and antigenically related variants thereof.

10. A synthetic polypeptide having an amino acid residue sequence, taken from left to right and in the direction of amino-terminus to carboxy-terminus, represented by the formula:

H-Gly-Gly-Gly-Ala-Gly-Gly-Ala-Gly-Ala-Gly-Gly-Gly-Ala-Gly-Ala-Gly-OH;

the pharmaceutically acceptable salts thereof, and antigenically related variants thereof.

11. A synthetic polypeptide having an amino acid residue sequence, taken from left to right and in the direction of amino-terminus to carboxy-terminus, represented by the formula:

H-Ala-Gly-Gly-Ala-Gly-Ala-Gly-Gly-Ala-Gly-Ala-Gly-OH;

the pharmaceutically acceptable salts thereof, and antigenically related variants thereof.

* * * * *

UNITED STATES PATENT AND TRADEMARK OFFICE
CERTIFICATE OF CORRECTION

PATENT NO. : 4,654,419

DATED : March 31, 1987

INVENTOR(S) : John H. Vaughan, et al.

It is certified that error appears in the above-identified patent and that said Letters Patent is hereby corrected as shown below:

In claim 6, lines 7-8, delete "anti-gencally" and insert --antigenically--

Signed and Sealed this

Fourteenth Day of June, 1988

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,654,419

DATED : March 31, 1987

INVENTOR(S) : John H. Vaughan et al.

It is certified that error appears in the above-identified patent and that said Letters Patent is hereby corrected as shown below:

Column 1, after the heading "TECHNICAL FIELD", insert the following paragraph:

--This invention was made with government support under Contract AM 21175 awarded by the National Institutes of Health. The government has certain rights in the invention.--

Signed and Sealed this

Eighteenth Day of January, 1994

Attest:

BRUCE LEHMAN

*Attesting Officer*  *Commissioner of Patents and Trademarks*